(12) United States Patent
Terracciano et al.

(10) Patent No.: US 9,320,740 B2
(45) Date of Patent: Apr. 26, 2016

(54) CEFTOLOZANE-TAZOBACTAM PHARMACEUTICAL COMPOSITIONS

(71) Applicant: Cubist Pharmaceuticals, Inc., Lexington, MA (US)

(72) Inventors: Joseph Terracciano, Concord, MA (US); Nicole Miller Damour, Belmont, MA (US); Chun Jiang, Hillsborough, CA (US); Giovanni Fogliato, Barzana (IT); Giuseppe Alessandro Donadelli, Casalpusterlengo (IT); Dario Resemini, Milan (IT)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days.

(21) Appl. No.: 14/214,221

(22) Filed: Mar. 14, 2014

(65) Prior Publication Data

US 2014/0262868 A1 Sep. 18, 2014

Related U.S. Application Data

(60) Provisional application No. 61/793,007, filed on Mar. 15, 2013, provisional application No. 61/792,092, filed on Mar. 15, 2013.

(51) Int. Cl.

| | |
|---|---|
| A61K 31/545 | (2006.01) |
| A61K 31/43 | (2006.01) |
| A61K 31/546 | (2006.01) |
| A61K 9/19 | (2006.01) |
| A61K 31/431 | (2006.01) |
| A61K 47/02 | (2006.01) |
| A61K 47/12 | (2006.01) |
| A61K 47/18 | (2006.01) |
| A61K 31/198 | (2006.01) |

(52) U.S. Cl.
CPC .............. *A61K 31/546* (2013.01); *A61K 9/19* (2013.01); *A61K 31/198* (2013.01); *A61K 31/43* (2013.01); *A61K 31/431* (2013.01); *A61K 47/02* (2013.01); *A61K 47/12* (2013.01); *A61K 47/183* (2013.01); *A61K 31/545* (2013.01)

(58) Field of Classification Search
CPC ... A61K 31/546; A61K 31/198; A61K 47/02; A61K 47/183; A61K 47/12; A61K 31/43; A61K 31/431; A61K 9/19; A61K 31/545
USPC .......................................... 514/192, 202, 207
See application file for complete search history.

(56) References Cited

U.S. PATENT DOCUMENTS

| | | |
|---|---|---|
| 4,200,575 A | 4/1980 | Numata et al. |
| 4,246,405 A | 1/1981 | Takaya et al. |
| 4,255,431 A | 3/1981 | Junggren et al. |
| 4,264,597 A | 4/1981 | Hashimoto et al. |
| 4,267,176 A | 5/1981 | Kamiya et al. |
| 4,268,509 A | 5/1981 | Teraji et al. |
| 4,284,631 A | 8/1981 | Takaya et al. |
| 4,291,031 A | 9/1981 | Takaya et al. |
| 4,298,529 A | 11/1981 | Ueda et al. |
| 4,299,829 A | 11/1981 | Kamiya et al. |
| 4,305,937 A | 12/1981 | Kamiya et al. |
| 4,327,093 A | 4/1982 | Ueda et al. |
| 4,331,665 A | 5/1982 | Teraji et al. |
| 4,332,798 A | 6/1982 | Teraji et al. |
| 4,332,800 A | 6/1982 | Teraji et al. |
| 4,336,253 A | 6/1982 | Lunn |
| 4,338,313 A | 7/1982 | Teraji et al. |
| 4,339,449 A | 7/1982 | Hashimoto et al. |
| 4,363,807 A | 12/1982 | Takaya et al. |
| 4,367,228 A | 1/1983 | Takaya et al. |
| 4,368,325 A | 1/1983 | Ueda et al. |
| 4,369,312 A | 1/1983 | Hashimoto et al. |
| 4,370,326 A | 1/1983 | Takaya et al. |
| 4,381,299 A | 4/1983 | Teraji et al. |
| 4,390,534 A | 6/1983 | Teraji et al. |
| 4,394,384 A | 7/1983 | Takaya et al. |
| 4,402,955 A | 9/1983 | Lunn |
| 4,405,617 A | 9/1983 | Takaya et al. |
| 4,407,798 A | 10/1983 | Kamiya et al. |
| 4,409,214 A | 10/1983 | Takaya et al. |
| 4,409,215 A | 10/1983 | Takaya et al. |
| 4,409,217 A | 10/1983 | Takaya et al. |
| 4,416,879 A | 11/1983 | Takaya et al. |
| 4,418,058 A | 11/1983 | Hirai et al. |
| 4,420,477 A | 12/1983 | Takaya et al. |

(Continued)

FOREIGN PATENT DOCUMENTS

| | | |
|---|---|---|
| AU | 614793 B1 | 5/1989 |
| AU | 707730 B2 | 5/1996 |

(Continued)

OTHER PUBLICATIONS

European Committee on Antimicrobial Sus Testing 2012.
Giske et al, 'Activity of Cephalosporin CXA-101 and Comparators against Extended-spectrum-beta-lactamase-producing Pseudomonas aeruginosa'. Journal of Antimicrobial Chemotherapy 2009, vol. 64, No. 2, pp. 430-431.
Jacqueline et al, 'Efficacy of Ceftolozane in a Murine Model of Pseudomonas aeruginosa acute pneumonia: in vivo Antimicrobial Activity and Impact on Host Inflammatory Response'. Journal of Antimicrobial Chemotherapy 2012, vol. 68, No. 1, pp. 1-7.
Livermore et al, 'Activity of Cephalosporin CXA-101 against Pseudomonas aeruginosa and Burkholderia cepacia strains and Isolates'. International Journal of Antimicrobial Agents 2009, vol. 34, No. 5, pp. 402-406.

(Continued)

*Primary Examiner* — My-Chau T Tran
(74) *Attorney, Agent, or Firm* — Lathrop & Gage LLP; Brian C. Trinque

(57) ABSTRACT

Pharmaceutical compositions are provided in unit dosage forms comprising ceftolozane and tazobactam in separate unit dosage form containers, ceftolozane prepared in the absence of tazobactam, tazobactam prepared in the absence of ceftolozane, and/or compositions where ceftolozane and tazobactam are first combined within a unit dosage form container.

21 Claims, 13 Drawing Sheets

(56) References Cited

U.S. PATENT DOCUMENTS

| | | |
|---|---|---|
| 4,423,213 A | 12/1983 | Takaya et al. |
| 4,425,340 A | 1/1984 | Teraji et al. |
| 4,425,341 A | 1/1984 | Takaya et al. |
| 4,427,677 A | 1/1984 | Takaya et al. |
| 4,430,499 A | 2/1984 | Wheeler |
| 4,431,642 A | 2/1984 | Teraji et al. |
| 4,436,912 A | 3/1984 | Wheeler |
| 4,438,113 A | 3/1984 | Takaya et al. |
| 4,443,443 A | 4/1984 | Ueda et al. |
| 4,443,444 A | 4/1984 | Takaya et al. |
| 4,447,429 A | 5/1984 | Teraji et al. |
| 4,450,270 A | 5/1984 | Lunn |
| 4,452,851 A | 6/1984 | Takaya et al. |
| 4,457,928 A | 7/1984 | Teraji et al. |
| 4,462,999 A | 7/1984 | Takaya et al. |
| 4,463,000 A | 7/1984 | Teraji et al. |
| 4,463,002 A | 7/1984 | Takaya et al. |
| 4,463,003 A | 7/1984 | Takaya et al. |
| 4,464,369 A | 8/1984 | Takaya et al. |
| 4,470,980 A | 9/1984 | Higuchi et al. |
| 4,474,779 A | 10/1984 | Nagano et al. |
| 4,477,447 A | 10/1984 | Ueda et al. |
| 4,487,768 A | 12/1984 | Takaya et al. |
| 4,495,182 A | 1/1985 | Teraji et al. |
| 4,496,562 A | 1/1985 | Takaya et al. |
| 4,499,088 A | 2/1985 | Takaya et al. |
| 4,501,739 A | 2/1985 | Lunn et al. |
| 4,515,788 A | 5/1985 | Takaya et al. |
| 4,521,413 A | 6/1985 | Teraji et al. |
| 4,529,592 A | 7/1985 | Micetich et al. |
| 4,546,101 A | 10/1985 | Takaya et al. |
| 4,550,102 A | 10/1985 | Teraji et al. |
| 4,559,334 A | 12/1985 | Takaya et al. |
| 4,562,073 A | 12/1985 | Micetich et al. |
| 4,563,449 A | 1/1986 | Teraji et al. |
| 4,577,014 A | 3/1986 | Lunn et al. |
| 4,584,290 A | 4/1986 | Takaya et al. |
| 4,585,872 A | 4/1986 | Teraji et al. |
| 4,590,186 A | 5/1986 | Takaya et al. |
| 4,600,772 A | 7/1986 | O'Callaghan et al. |
| 4,608,373 A | 8/1986 | Shibanuma et al. |
| 4,609,730 A | 9/1986 | Takaya et al. |
| 4,616,083 A | 10/1986 | Shima et al. |
| 4,622,318 A | 11/1986 | Takaya et al. |
| 4,626,384 A | 12/1986 | Tanaka et al. |
| 4,631,274 A | 12/1986 | Takaya et al. |
| 4,640,915 A | 2/1987 | Hashimoto et al. |
| 4,647,556 A | 3/1987 | Lattrell et al. |
| 4,667,028 A | 5/1987 | Schwab et al. |
| 4,690,921 A | 9/1987 | Shibanuma et al. |
| 4,692,443 A | 9/1987 | Katner |
| 4,698,337 A | 10/1987 | Takaya et al. |
| 4,699,980 A | 10/1987 | Shibanuma et al. |
| 4,703,046 A | 10/1987 | Ueda et al. |
| 4,705,851 A | 11/1987 | Takaya et al. |
| 4,735,937 A | 4/1988 | Heusler et al. |
| 4,748,172 A | 5/1988 | Katner |
| 4,761,410 A | 8/1988 | Takaya et al. |
| 4,764,606 A | 8/1988 | Imai et al. |
| 4,769,183 A | 9/1988 | Kawamata et al. |
| 4,808,617 A | 2/1989 | Kaplan et al. |
| 4,808,711 A | 2/1989 | Shimizu et al. |
| 4,822,785 A | 4/1989 | Ishibashi et al. |
| 4,822,787 A | 4/1989 | Murata et al. |
| 4,833,134 A | 5/1989 | Kishimoto et al. |
| 4,861,769 A | 8/1989 | Takaya et al. |
| 4,868,174 A | 9/1989 | Takaya et al. |
| 4,871,730 A | 10/1989 | Takaya et al. |
| 4,882,434 A | 11/1989 | Yoshioka |
| 4,921,852 A | 5/1990 | Murata et al. |
| 4,923,857 A | 5/1990 | Murata et al. |
| 4,925,934 A | 5/1990 | Taniguchi et al. |
| 4,927,818 A | 5/1990 | Takaya et al. |
| 4,935,507 A | 6/1990 | Takaya et al. |
| 4,943,567 A | 7/1990 | Nishizawa et al. |
| 4,952,578 A | 8/1990 | Sakane et al. |
| 4,960,766 A | 10/1990 | Takaya et al. |
| 4,963,543 A | 10/1990 | Murata et al. |
| 4,963,544 A | 10/1990 | Murata et al. |
| 4,971,962 A | 11/1990 | Oh et al. |
| 4,982,596 A | 1/1991 | Peterson et al. |
| 5,036,064 A | 7/1991 | Gotschi |
| RE33,778 E | 12/1991 | Iwanami et al. |
| 5,071,979 A | 12/1991 | Lattrell et al. |
| 5,073,550 A | 12/1991 | Gotschi |
| 5,081,116 A | 1/1992 | Nagano et al. |
| 5,095,012 A | 3/1992 | Okita et al. |
| 5,102,877 A | 4/1992 | Murata et al. |
| 5,104,866 A | 4/1992 | Sakane et al. |
| 5,108,997 A | 4/1992 | Takaya et al. |
| 5,109,130 A | 4/1992 | Sakane et al. |
| 5,138,066 A | 8/1992 | Gotschi |
| 5,159,070 A | 10/1992 | Heymes et al. |
| 5,162,520 A | 11/1992 | Takaya et al. |
| 5,173,485 A | 12/1992 | Sakane et al. |
| 5,179,485 A | 1/1993 | Tamayama |
| 5,187,160 A | 2/1993 | Sakane et al. |
| 5,210,080 A | 5/1993 | Takaya et al. |
| 5,215,982 A | 6/1993 | Sakane et al. |
| 5,215,983 A | 6/1993 | Murata et al. |
| 5,219,848 A | 6/1993 | Hennequin et al. |
| 5,234,920 A | 8/1993 | Okita et al. |
| 5,244,890 A | 9/1993 | Yamanaka et al. |
| 5,281,589 A | 1/1994 | Kim et al. |
| 5,286,721 A | 2/1994 | Murata et al. |
| 5,319,140 A | 6/1994 | Gotschi |
| 5,329,002 A | 7/1994 | Albrecht et al. |
| 5,336,768 A | 8/1994 | Albrecht et al. |
| 5,366,970 A | 11/1994 | Sakane et al. |
| 5,389,627 A | 2/1995 | Kim et al. |
| 5,498,787 A | 3/1996 | Wang et al. |
| 5,523,400 A | 6/1996 | Wei et al. |
| 5,637,580 A | 6/1997 | White et al. |
| 5,646,139 A | 7/1997 | White et al. |
| 5,648,346 A | 7/1997 | White et al. |
| 5,656,623 A | 8/1997 | White et al. |
| 5,661,144 A | 8/1997 | Tsushima et al. |
| 5,663,163 A | 9/1997 | Takaya et al. |
| 5,763,603 A | 6/1998 | Trickes |
| 6,207,661 B1 | 3/2001 | Thompson et al. |
| 6,214,818 B1 | 4/2001 | Nishitani et al. |
| 6,235,311 B1 | 5/2001 | Ullah et al. |
| 6,458,950 B1 | 10/2002 | Nishitani et al. |
| 6,518,263 B1 | 2/2003 | Nishitani et al. |
| 6,660,855 B2 | 12/2003 | Shimabayashi et al. |
| 6,774,104 B1 | 8/2004 | Sawai et al. |
| 6,800,621 B2 | 10/2004 | Nishitani et al. |
| 6,878,686 B2 | 4/2005 | Marquess et al. |
| 6,936,711 B2 | 8/2005 | Deshpande et al. |
| 6,974,797 B2 | 12/2005 | Fatheree et al. |
| 6,995,138 B2 | 2/2006 | Marquess et al. |
| 7,067,481 B2 | 6/2006 | Fatheree et al. |
| 7,067,482 B2 | 6/2006 | Fatheree et al. |
| 7,112,565 B2 | 9/2006 | Sawai et al. |
| 7,129,232 B2 | 10/2006 | Ohki et al. |
| 7,179,801 B2 | 2/2007 | Ohki et al. |
| 7,192,943 B2 | 3/2007 | Yamanaka et al. |
| 7,273,935 B2 | 9/2007 | Deshpande et al. |
| 7,279,458 B2 | 10/2007 | Fatheree et al. |
| 7,304,075 B2 | 12/2007 | Araki et al. |
| 7,332,471 B2 | 2/2008 | Fatheree et al. |
| 7,341,993 B2 | 3/2008 | Fatheree et al. |
| 7,378,408 B2 | 5/2008 | Kimball et al. |
| 7,384,928 B2 | 6/2008 | Nishitani et al. |
| 7,417,143 B2 | 8/2008 | Gnanaprakasam et al. |
| 7,547,777 B2 | 6/2009 | Tokumaru et al. |
| 7,553,962 B2 | 6/2009 | Fatheree et al. |
| 7,601,690 B2 | 10/2009 | Fatheree et al. |
| 7,612,037 B2 | 11/2009 | Fatheree et al. |
| 7,649,080 B2 | 1/2010 | Fatheree et al. |
| 7,655,621 B2 | 2/2010 | Fatheree et al. |
| 7,674,898 B2 | 3/2010 | Shimabayashi et al. |
| 7,728,127 B2 | 6/2010 | Fatheree et al. |
| 7,842,683 B2 | 11/2010 | Koppel |

(56) References Cited

U.S. PATENT DOCUMENTS

| | | | |
|---|---|---|---|
| 7,915,229 B2 | 3/2011 | Cohen et al. | |
| 8,133,883 B2 | 3/2012 | Cohen et al. | |
| 8,476,425 B1 | 7/2013 | Lai et al. | |
| 8,906,898 B1 * | 12/2014 | Hwang | C07D 501/60 514/210.05 |
| 8,968,753 B2 * | 3/2015 | Terracciano | A61K 9/19 424/400 |
| 9,044,485 B2 | 6/2015 | Terracciano et al. | |
| 2002/0115650 A1 | 8/2002 | Glinka | |
| 2002/0193587 A1 | 12/2002 | Shimabayashi et al. | |
| 2003/0130173 A1 | 7/2003 | Fatheree et al. | |
| 2003/0232983 A1 | 12/2003 | Deshpande et al. | |
| 2005/0171077 A1 | 8/2005 | Ruppen et al. | |
| 2005/0228176 A1 | 10/2005 | Gnanaprakasam et al. | |
| 2006/0051412 A1 | 3/2006 | Petereit et al. | |
| 2006/0084639 A1 | 4/2006 | Cohen et al. | |
| 2006/0099253 A1 | 5/2006 | Becker et al. | |
| 2006/0173177 A1 | 8/2006 | Gego et al. | |
| 2006/0241017 A1 | 10/2006 | Chandran | |
| 2006/0269485 A1 | 11/2006 | Friedman et al. | |
| 2006/0287244 A1 | 12/2006 | Chandran | |
| 2006/0293516 A1 | 12/2006 | Wada et al. | |
| 2007/0054899 A1 | 3/2007 | Park et al. | |
| 2007/0116770 A1 | 5/2007 | Garms et al. | |
| 2007/0219191 A1 | 9/2007 | Nishitani et al. | |
| 2007/0286817 A1 | 12/2007 | Tatapudy et al. | |
| 2007/0286818 A1 | 12/2007 | Tatapudy et al. | |
| 2008/0015156 A1 | 1/2008 | Udayampalayam Palanisamy et al. | |
| 2008/0103121 A1 | 5/2008 | Gole et al. | |
| 2008/0160067 A1 | 7/2008 | Boeckh et al. | |
| 2008/0233196 A1 | 9/2008 | Cattaneo et al. | |
| 2009/0098088 A1 | 4/2009 | Taylor et al. | |
| 2009/0137460 A1 | 5/2009 | Marquess et al. | |
| 2009/0155387 A1 | 6/2009 | Zhang | |
| 2009/0156517 A1 | 6/2009 | Zhang | |
| 2009/0156518 A1 | 6/2009 | Zhang | |
| 2009/0186865 A1 | 7/2009 | Diago et al. | |
| 2009/0227554 A1 | 9/2009 | Liversidge et al. | |
| 2009/0274662 A1 | 11/2009 | Magowan et al. | |
| 2009/0275552 A1 | 11/2009 | Patel et al. | |
| 2009/0291102 A1 | 11/2009 | Fortin | |
| 2009/0311234 A1 | 12/2009 | Koski et al. | |
| 2010/0040548 A1 | 2/2010 | Yu | |
| 2010/0286031 A1 | 11/2010 | Charan et al. | |
| 2011/0044917 A1 | 2/2011 | Tosetti | |
| 2011/0136763 A1 | 6/2011 | Xia et al. | |
| 2011/0190252 A1 | 8/2011 | Watson et al. | |
| 2011/0257079 A1 | 10/2011 | Chaudhary et al. | |
| 2013/0065874 A1 | 3/2013 | Chandorkar et al. | |
| 2014/0187528 A1 * | 7/2014 | Lai | A61K 31/155 514/192 |
| 2014/0206659 A1 | 7/2014 | Lai et al. | |
| 2014/0213567 A1 | 7/2014 | Lai et al. | |
| 2014/0262868 A1 | 9/2014 | Terracciano et al. | |
| 2014/0274989 A1 | 9/2014 | Terracciano et al. | |
| 2014/0274990 A1 | 9/2014 | Terracciano et al. | |
| 2014/0274991 A1 | 9/2014 | Damour et al. | |
| 2014/0274992 A1 | 9/2014 | Damour et al. | |
| 2014/0274993 A1 | 9/2014 | Terracciano et al. | |
| 2014/0274994 A1 | 9/2014 | Damour et al. | |
| 2014/0274995 A1 | 9/2014 | Zhou et al. | |
| 2014/0274996 A1 | 9/2014 | Damour et al. | |
| 2014/0274997 A1 | 9/2014 | Zhou et al. | |
| 2014/0274998 A1 | 9/2014 | Terracciano et al. | |
| 2014/0275000 A1 | 9/2014 | Damour et al. | |
| 2014/0303136 A1 | 10/2014 | Terracciano et al. | |
| 2014/0309205 A1 | 10/2014 | Terracciano et al. | |
| 2015/0045336 A1 | 2/2015 | Jiang et al. | |
| 2015/0072968 A1 * | 3/2015 | Krishna | A61K 31/546 514/192 |
| 2015/0094293 A1 * | 4/2015 | Jurkauskas | C07D 501/60 514/192 |
| 2015/0150883 A1 | 6/2015 | Jiang et al. | |

FOREIGN PATENT DOCUMENTS

| | | |
|---|---|---|
| AU | 2002952355 | 10/2002 |
| AU | 2003904813 | 9/2003 |
| AU | 2003905084 | 9/2003 |
| CA | 1235689 A1 | 4/1988 |
| CA | 2140701 A1 | 7/1995 |
| CN | 1236781 A | 12/1999 |
| CN | 101434610 A | 5/2009 |
| CN | 101696212 A | 4/2010 |
| CN | 102020663 A | 4/2011 |
| CN | 102382123 A | 3/2012 |
| EP | 0047977 B1 | 9/1981 |
| EP | 0097446 A1 | 1/1984 |
| EP | 0137440 | 4/1985 |
| EP | 0137442 A2 | 4/1985 |
| EP | 0138552 | 4/1985 |
| EP | 0111934 B1 | 8/1988 |
| EP | 0318767 A2 | 6/1989 |
| EP | 0664117 A1 | 7/1995 |
| EP | 0711774 B1 | 5/1996 |
| EP | 1273586 A1 | 1/2003 |
| EP | 1285923 A1 | 2/2003 |
| EP | 1468697 A1 | 10/2004 |
| EP | 1134222 B1 | 4/2005 |
| EP | 1554287 | 7/2005 |
| EP | 1671974 A1 | 6/2006 |
| EP | 1686131 A2 | 8/2006 |
| EP | 1759697 A1 | 3/2007 |
| EP | 1787641 A1 | 5/2007 |
| EP | 1959933 | 8/2008 |
| EP | 1974721 A1 | 10/2008 |
| EP | 2015755 | 1/2009 |
| EP | 2062581 A1 | 5/2009 |
| EP | 2062582 A1 | 5/2009 |
| EP | 2062585 A1 | 5/2009 |
| EP | 2136844 | 12/2009 |
| EP | 2305251 A2 | 4/2011 |
| EP | 1154770 | 11/2011 |
| JP | 62103092 A | 5/1987 |
| JP | 62158290 A | 7/1987 |
| JP | 63051388 A | 3/1988 |
| JP | 63051389 A | 3/1988 |
| JP | 2088582 A | 3/1990 |
| JP | 2117678 A | 5/1990 |
| JP | 4288086 A | 10/1992 |
| JP | 5222058 A | 8/1993 |
| JP | 6056848 A | 3/1994 |
| JP | 6128268 A | 5/1994 |
| JP | 2005162670 A | 6/2005 |
| WO | 9512601 A1 | 5/1995 |
| WO | WO 99/28308 | 6/1999 |
| WO | WO 99/64049 | 12/1999 |
| WO | WO0004915 A1 | 2/2000 |
| WO | 0050035 A2 | 8/2000 |
| WO | 02090363 A1 | 11/2002 |
| WO | 02092605 A1 | 11/2002 |
| WO | 02102378 A1 | 12/2002 |
| WO | 03066053 A1 | 8/2003 |
| WO | WO 03/078440 | 9/2003 |
| WO | 03104241 A1 | 12/2003 |
| WO | 2004019901 A1 | 3/2004 |
| WO | 2004039776 A2 | 5/2004 |
| WO | WO 2004/048551 | 6/2004 |
| WO | 2004066976 A1 | 8/2004 |
| WO | 2004098643 A1 | 11/2004 |
| WO | WO 2005/005436 | 1/2005 |
| WO | 2005074925 A1 | 8/2005 |
| WO | 2006044600 A1 | 4/2006 |
| WO | 2006045006 A1 | 4/2006 |
| WO | 2006088305 A1 | 8/2006 |
| WO | 2007065862 A1 | 6/2007 |
| WO | 2007086011 A1 | 8/2007 |
| WO | 2007086013 A1 | 8/2007 |
| WO | 2007086014 A1 | 8/2007 |
| WO | 2007099396 A2 | 9/2007 |
| WO | 2007129176 A2 | 11/2007 |
| WO | 2007145866 A1 | 12/2007 |
| WO | 2007145868 A1 | 12/2007 |

(56) References Cited

FOREIGN PATENT DOCUMENTS

| | | | |
|---|---|---|---|
| WO | 2008030469 | A2 | 3/2008 |
| WO | 2008065247 | A1 | 6/2008 |
| WO | 2008075207 | A2 | 6/2008 |
| WO | 2008101743 | A2 | 8/2008 |
| WO | 2008113177 | A1 | 9/2008 |
| WO | 2009048603 | A1 | 4/2009 |
| WO | WO 2009/105782 | | 8/2009 |
| WO | 2009122252 | A2 | 10/2009 |
| WO | 2009134948 | A1 | 11/2009 |
| WO | 2010014285 | A1 | 2/2010 |
| WO | 2010142241 | A1 | 12/2010 |
| WO | 2011101710 | A1 | 8/2011 |
| WO | 2011112435 | A1 | 9/2011 |
| WO | 2011127200 | A2 | 10/2011 |
| WO | W02013036783 | A2 | 3/2013 |
| WO | 2014/052799 | | 4/2014 |

OTHER PUBLICATIONS

Titelman et al, 'In vitro Activity of CXA-101 Plus Tazobactum

Takeda et al, 'Stability of FR264205 against AmpC beta-lactamase of Pseudomonas aeruginoas'. International Journal Antimicrobial Agents, 2007. vol. 30, No. 5, pp. 443-445.

Takeda et al., In vitro and in vivo activities of a new cephalosporin, FR264205, against Pseudomonas aeruginosa. Antimicrob Agents Chemother. 2007; 51(3):826-30. against CTX-M-14 and CTX-M-15-producing *Escherichia* and Klebsiella pneumoniae'. Diagnostic Microbiology and Infectious Disease. 2011, vol. 70, No. 1, pp. 137-141.

Toda et al, Synthesis and SAR of Novel Parenteral Anti-pseudomonal cephalosporins: Discovering of FR264205. Med Chem Lett. 2008, vol. 18, No. 17, pp. 4849-4852.

Abstract for Brown et al. Activity profile of CXA-101 against gram-positive and gram-negative pathogens by broth and agar dilution. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-354; This poster is obtainable at: http://www.eurofins.com/media/694466/Calixe/020F1-354%20broth%20agar%20v6.pdf.

Abstract for Brown et al. Activity profile of CXA-101 and CXA-101/tazobactam against target gram-positive and gram-negative pathogens. 49th Annual Interscience Conference on Antimicrobial Agents and Chemotherapy (ICAAC 2009); 12-15, 2009. Poster F1-1986; This poster is obtainable at: http://www.eurofins.com/media/767069/Final%20F1-1986.pdf.

Abstract for Brown et al. Effect of various testing parameters on the activity of CXA-101 by broth microdilution. 48th Annual Interscience Conference on Antimicrobial Agents and Chemotherapy & the Infectious Disease Society of America 46th Annual Meeting (ICAAC/IDSA 2008): Oct. 25-28, 2008. Poster F1-357; This poster is obtainable at: http://www.eurofins.com/media/694469/CW/020F1-357%20parameter%20v6.pdf.

Abstract for Brown et al. Mode of action of CXA-101 based on minimum bactericidal concentration analysis and time-kill kinetic analysis. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-358; This poster is obtainable at: http://www.eurofins.com/media/694472/CXA%20F1-358°/020tV/020mbe/020v5.pdf.

Abstract for Brown et al., Disk diffusion testing of CXA-101 and CXA-101 in combination with tazobactam against target pathogens. 49th Annual Interscience Conference on Antimicrobial Agents and Chemotherapy (ICAAC 2009); 12th-15th, 2009. Poster F1-1998; This poster is obtainable at: http://www.eurofins.com/media/767072/Final%20F1-1998.pdf.

Abstract for Brown et al., Quality control parameters for CXA-101 broth microdilution susceptibility tests. 49th Annual Interscience Conference on Antimicrobial Agents and Chemotherapy (ICAAC 2009); Sep. 12-15, 2009. Poster F1-1997.

Abstract for Bulik et al. In vivo Comparison of CXA-101 (FR264205) with and without Tazobactam verus Piperacillin-Tazobactam Using Human Simulated Exposures against Phenotypically Diverse Gram-Negative Organisms. ICAAC 2010. Poster A1-1381; This poster is obtainable at: http://www.cubist.com/downloads/Bulik_PP_ICAAC_2010_in_vivo_CXA-101_vs_TZP_against_gram_neg.pdf.

Abstract for Cabot et al. Activity of CXA-101 Against a Large Collection of P. aeruginosa Blood Stream Isolates Overexpressing AmpC and the Major Efflux Pumps. 50th Annual Interscience Conference on Antimicrobial Agents and Chemotherapy (ICAAC 2010); Sep. 12-15, 2010. Poster E-816.

Abstract for Chandorkar et al. Penetration of Ceftolozane/Tazobactam and Piperacillin/Tazobactam into the Epithelial lining of Fluid of Healthy Volunteers. 22nd Annual Meeting of the European Congress of Clinical Microbiology (ECCMID 2012); Mar. 31-Apr. 3, 2012. Poster P1627.

Abstract for Chandorkar et al. Intrapulmonary penetration of CXA-201 and Piperacillin/tazobactam in healthy adult subjects. 49th Annual Meeting of the Infectious Diseases Society of America (IDSA 2011); Oct. 20-23, 2011. Poster 611.

Abstract for Craig et al., In vivo activity Of Cxa-101 plus a 2:1, 4:1, or 8:1 ratio of tazobactam against various Enterobacteriaceae producing Extended-spectrum beta-lactamases in the thighs of neutropenic mice. 49th Annual Interscience Conference on Antimicrobial Agents and Chemotherapy (ICAAC 2009); Sep. 12-15, 2009. Poster F1-1999.

Abstract for Craig et al., In vivo activity of CXA-101, a new cephalosporin, against Pseudomonas aeruginosa and other Enterobacteriaceae in the thighs of neutropenic mice. 49th Annual Interscience Conference on Antimicrobial Agents and Chemotherapy (ICAAC 2009); Sep. 12-15, 2009. Poster F1-2002.

Abstract for Fenneteau et al. Population PK/PD Modeling and Simulations of a Fixed-Dose Combination of CXA-101 and Tazobactam to Optimize Dosing Strategies in Renally Impaired Patients with Complicated Urinary Tract Infection. 3rd Biennial American Conference on Pharmacometrics (ACoP 2011); Apr. 3-6, 2011; This poster is obtainable at: http://www.go-acop.org/sites/default/files/webform/posters/ACOP2011%20-%20Dosing%20Strategies%20of%20CXA-101%20and%20Taz%20in%020cUTI%020Patients.pdf.

Abstract for Ge et al., CXA-101 population PK analysis and Monte Carlo simulation for PK/PD target attainment and dose regimen selection. 49th Annual Interscience Conference on Antimicrobial Agents and Chemotherapy (ICAAC 2009); Sep. 12-15, 2009. Poster F1-2003.

Abstract for Ge et al., PK and safety of CXA-101, a new anti-pseudomonal cephalosporin, in healthy adult subjects after single intravenous dosing. 49th Annual Interscience Conference on Antimicrobial Agents and Chemotherapy (ICAAC 2009); Sep. 12-15, 2009. Poster F1-2004.

Abstract for Ge et al., PK study of CXA-101 in combination with tazobactam in dogs after intravenous administration. 49th Annual Interscience Conference on Antimicrobial Agents and Chemotherapy (ICAAC 2009); Sep. 12-15, 2009. Poster F1-2001.

Abstract for Giske et al., CXA-101 has high activity against clinical isolates of Pseudomonas aeruginosa including ceftazidime-resistant isolates. 49th Annual Interscience Conference on Antimicrobial Agents and Chemotherapy (ICAAC 2009); Sep. 12-15, 2009. Poster F1-1988.

Abstract for Hershberger et al. CXA-101/Tazobactam Probability of Target Attainment Using Population Pharmacokinetic Analysis. Joint Meeting of the European Congress of Clinical Microbiology and Infectious Diseases and International Congress of Chemotherapy (ECCMID-ICC 2011); May 7-12, 2011. Poster 1520; This poster is obtainable at: http://www.poster-submission.com/search/sresult.

Abstract for Jacqueline . Assessment of the In vivo Activity of CXA-101 in a Murine Model of Pseudomonas aeruginosa Pneumonia: Comparison with Ceftazidime and Piperacillin-Tazobactam. 50th Annual Interscience Conference on Antimicrobial Agents and Chemotherapy (ICAAC 2010); Sep. 12-15, 2010. Poster B-1401.

Abstract for Jacqueline et al. 50% effective dose determination of CXA-101 alone or in combination with tazobactam for treating

(56) References Cited

OTHER PUBLICATIONS experimental peritonitis in mice due to extended-spectrum beta-lactamase-producing *Escherichia coli* strains: comparison with ceftazidime and piperacillin/tazobactam. 49th Annual Interscience Conference on Antimicrobial Agents and Chemotherapy (ICAAC 2009); Sep. 12-15, 2009. Poster F1-2000.

Abstract for Jacqueline et al. FIC Index determination of CXA-101/tazobactam in combination with amikacin, aztreonam, meropenem, levofloxacin, and tigecycline against *Escherichia coli*, Klebsiella pneumoniae, and Pseudomonas aeruginosa strains. 49th Annual Interscience Conference on Antimicrobial Agents and Chemotherapy (ICAAC 2009); Sep. 12-15, 2009. Poster F1-1995.

Abstract for Jacqueline et al. In vitro assessment using time-kill curves of CXA-101/tazobactam against *Escherichia coli*, Klebsiella pneumoniae, and Pseudomonas aeruginosa strains. 49th Annual Interscience Conference on Antimicrobial Agents and Chemotherapy (ICAAC 2009); Sep. 12-15, 2009. Poster F1-1996.

Abstract for Juan et al., Oliver A. Activity of the new cephalosporin CXA-101 against carbapenem-resistant Pseudomonas aeruginosa isolates from a Spanish multicenter study. 49th Annual Interscience Conference on Antimicrobial Agents and Chemotherapy (ICAAC 2009); Sep. 12-15, 2009. Poster F1-1987.

Abstract for Killian et al. An Equivalency Study of a Sensititre Dried MIC Plate Compared with the CLSI Broth Microdilution Reference Method for CXA-201 and Comparator Antimicrobials. 51st Annual Interscience Conference on Antimicrobial Agents and Chemotherapy (ICAAC 2011); Sep. 17-20, 2011. Poster D-691A.

Abstract for Livermore et al., Warner M. Activity of cephalosporin CXA-101 vs. P. aeruginosa. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-355; This poster is obtainable at: http://www.hpa.org.uk/webc/HPAwebFile/HPAweb_C/1225354148015.

Abstract for Marier et al. Pharmacokinetics of a novel anti-pseudomonal cephalosporin, CXA-101, and tazobactam in healthy adult subjects. 50th Annual Interscience Conference on Antimicrobial Agents and Chemotherapy (ICAAC 2010); Sep. 12-15, 2010. Poster A1-1391.

Abstract for Marier et al. Population PK Analysis of Intravenous CXA-101 in Subjects with Complicated Urinary Tract Infection, Including Pyelonephritis. 112th Annual Meeting of the American Society for Clinical Pharmacology and Therapeutics (ASCPT 2011); Mar. 2-5, 2011. Poster PII-49.

Abstract for Hershberger et al. Pharmacokinetics of CXA-101/tazobactam in Subjects with Mild or Moderate Renal Impairment. Joint Meeting of the European Congress of Clinical Microbiology and Infectious Diseases and International Congress of Chemotherapy (ECCMID-ICC 2011); May 7-12, 2011. Poster 1519; This poster is obtainable at: http://www.poster-submission.com.

Abstract for Miller et al. Probability of Target Attainment of CXA-201 in Patients with Renal Hyperclearance. 49th Annual Meeting of the Infectious Diseases Society of America (IDSA 2011); Oct. 20-23, 2011. Poster B1-589.

Abstract for Miller et al., Safety and Pharmacokinetics of Intravenous Ceftolozane/tazobactam 3 g every 8 Hours and Cumulative Fraction of Response in Plasma and Epithelial Lining Fluid in a Simulated Ventilator Associated Pneumonia Population. 52nd Annual Interscience Conference on Antimicrobia Agents and Chemotherapy (ICAAC 2012); Sep. 9-12, 2012. Poster A-641.

Abstract for Moulds et al., Impact of characterized resistance mechanisms on the susceptibility of Pseudomonas aeruginosa to CXA-101. 50th Annual Interscience Conference on Antimicrobial Agents and Chemotherapy (ICAAC Sep. 12-15, 2010. Poster C1-1415; This poster is obtainable at: http://www.cubist.com/downloads/Moulds.PP.ICAAC_2010.Impact_of_resis_mech_on_suscep_of_P_aeruginosa_to_CXA_JNS.pdf.

Abstract for Moya et al. Affinity of the new cephalosporin CXA-101 to penicillin-binding proteins of Pseudomonas aeruginosa. 49th Annual Interscience Conference on Antimicrobial Agents and Chemotherapy (ICAAC 2009); Sep. 12-15, 2009. Poster F1-1985.

Abstract for Moya et al. Pan-Beta-lactam resistance development in P. aeruginosa clinical strains: molecular mechanisms, PBPs profiles and binding affinities. 51st Annual Interscience Conference on Antimicrobial Agents and Chemotherapy (ICAAC 2011); Sep. 17-20, 2011. Poster C1-619.

Abstract for Mushtaq et al. Activity of cephalosporin CXA-101 with B-lactamase inhibitors vs. Enterobacteriaceae. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-356; This poster is obtainable at: http://www.hpa.org.uk/webc/HPAwebFile/HPAweb_C/1225354148047.

Abstract for Riera et al. Activity of the new cephalosporin CXA-101 against biofilms of relevant P. aeruginosa phenotypes in cystic fibrosis chronic respiratory infection: mucoid and hypermutable strains. 49th Annual Interscience Conference on Antimicrobial Agents and Chemotherapy (ICAAC 2009); Sep. 12-15, 2009. Poster F1-1990.

Abstract for Sader et al., Activity of the Novel Antimicrobial Ceftolozane)Tazobactam Tested Against Bacterial Isolates in USA Hospitals from Patients with Pneumonia (2011). IDWeek 2012: A Joint Meeting of IDSA, SHEA, HIVMA, and PIDS; Oct. 17-21, 2012. Poster 846; This poster is obtainable at: http://www.jmilabs.com/data/posters/IDWeek2012/846. Pdf.

Abstract for Sader et al., Activity of the Novel Antimicrobial Ceftolozanefrazobactam Tested Against Contemporary Clinical Strains from USA Hospitals (2011). 52nd Annual Interscience Conference on Antimicrobial Agents and Chemotherapy (Icaac 2012); Sep. 9-12, 2012. Poster E-199.

Abstract for Sader et al., Activity of the Novel Antimicrobial CXA-201 Tested Against Contemporary Clinical Strains from European Hospitals. 22nd Annual Meeting of the European Congress of Clinical Microbiology (ECCMID 2012); Mar. 31-Apr. 3, 2012. Poster P1446.

Abstract for Sader et al., Activity of the novel cephalosporin CXA-101 tested in combination with tazobactam against cephalosporin-resistant Enterobacteriaceae, P. aeruginosa and B. fragilis. 49th Annual Interscience Conference on Antimicrobial Agents and Chemotherapy (ICAAC 2009); Sep. 12-15, 2009. Poster F1-1992; This poster is obtainable at: http://www.jmilabs.com/data/posters/ICAAC2009/F1-1992.pdf.

Abstract for Snydman et al., Activity of Ceftolozane/Tazobactam CXA-201 against 270 recent isolates from the bacteroides group. 22nd Annual Meeting of the European Congress of Clinical Microbiology (ECCMID 2012); Mar. 31-Apr. 3, 2012. Poster; This poster is obtainable at: http://www.escmid_orgtescmid_library/online_lecture_library/?search=l&current_page=l&search_term=snydman.

Abstract for Soon et al., In vitro Pharmacodynamics of CXA-201 (Ceftolozane/Tazobactam) against Beta-lactamase Producing *Eschericia coli*. 52nd Annual Interscience Conference on Antimicrobial Agents and Chemotherapy (ICAAC 2012); Sep. 9-12, 2012. Poster E-201.

Abstract for Titelman et al. Activity of CXA-101 plus tazobactam against ESBL-producing *E. coli* and K. pneumoniae. 49th Annual Interscience Conference on Antimicrobial Agents and Chemotherapy (ICAAC 2009); Sep. 12-15, 2009. Poster F1-1993.

Abstract for Umeh et al., A double-blind, randomized, phase 2 study to compare the safety and efficacy of intravenous CXA-101 and intravenous ceftazidime in complicated urinary tract infection. 50th Annual Interscience Conference on Agents and Chemotherapy (ICAAC 2010); Sep. 12-15, 2010. Poster L1-361A; This poster is obtainable at: http://www.cubist.com/downloads/Umeh_ICAAC2010_08144v2.pdf.

Abstract for Walkty et al. In Vitro Activity of Ceftolozane/Tazobactam (CXA-201) versus Pseudomonas aeruginosa Isolates Obtained from Patients in Canadian Hospitals: CANWARD 2011. IDWeek 2012: A Joint Meeting of IDSA, SHEA, HIVMA, and PIDS; Oct. 17-21, 2012. Poster 1616; This poster is obtainable at: https://idsa.confex.com/idsa/2012/webprogram/Handouttid509/POSTER202_1616.pdf.

Abstract for Zamorano et al. Activity of the new cephalosporin CXA-101 against P. aeruginosa isolates from chronically infected cystic

(56) References Cited

OTHER PUBLICATIONS fibrosis patients. 49th Annual Interscience Conference on Antimicrobial Agents and Chemotherapy (ICAAC 2009); Sep. 12-15, 2009. Poster F1-1991.
Abstract for Zhanel et al., In vitro Activity of Ceftolozane/tazobactam Tested Against 1,705 Gram-Negative Pathogens Isolated from Patients in Canadian Hospitals in 2011: CANWARD Surveillance Study. 52nd Annual Interscience Conference on Antimicrobial Agents and Chemotherapy (ICAAC 2012); Sep. 9-12, 2012. Poster E-200.
Anderegg et al: Quality Control Guidelines for BAL9141 (Ro 63/9141), an Investigational Cephalosporin, When Reference MIC and Standardized Disk Diffusion Susceptibility Test Methods Are Used; Journal of Clinical Microbiology. (2004), pp. 3356-3358.
Farrell: Antimicrobial Activity of Ceftolozane-Tazobactam Tested against Enterobacteriaceae with Various Resistance Patterns Isolated in U.S. Hospitals; Antimicrobial Agents and Chemotherapy; (2013) vol. 57 No. 12 pp. 6305-6310.
International Preliminary Report on Patentability for for PCT/US2012/054191, dated Mar. 12, 2014,8 pages.
International Search Report for PCT/US2012/054191, dated Feb. 20, 2013, 4 pages.
Marunaka: Degradation of beta-lactamase inhibitor, (2S,3R,5S)-3-methyl-7-oxo-3-(1H-1,2,3-triazol-1-yl-methyl)-4-thia-1-azabicyclo[3.2.0]heptane-2-carboxylic acid 4,,4-dioxide (YTR-830H), in Aqueous Solutions and Alkaline MEthanol Solution: Pathway and Structural Elucidation of Products; Chem. Pharm. Bull.; 1988, vol. 36, pp. 4478-4487.
Matsushima: Degradation of beta-lactamase inhibitor, (2S,3R,5S)-3-methyl-7-oxo-3-(1H-1,2,3-triazol-1-yl-methyl)-4-thia-1-azabicyclo[3.2.0]heptane-2-carboxylic acid 4,,4-dioxide (YTR-830H) in Solid State: Structural Eldcidation; Chem. Pharm. Bull.; 1988, vol. 36, pp. 4593-4596.
Murano: Structural requirements for the stability of novel cephalosporins to AmpC beta-lactamase based on 3-D structure; Bioorg. Med. Chem. Lett.; 2007, vol. 16, pp. 2261-2275.
Search Request Confirmation; Science IP; Dec. 6, 2010, 3 pages.
Sutcliffe et al: Multidrug-Resistant Gram-Negative Pathogens: New Strategies; Tetraphase Pharmaceuticals . Retrieved online from: http://www.tufts.edu/med/apua/practitioners/resources_23_2817980013.pdf Retrieved Mar. 19, 2014.
U.S. National Institutes of Health, 'Safety and Efficacy Study of Ceftolozane/Tazobactam to Treat Ventilated Nosocomial Pneumonia (ASPECT-NP)'. Sponsored by Cubist Pharmaceuticals. http://www.clinicaltrials.gov/ct2/show/NCT02070757?term=ceftolozane &rank=1 Updated Feb. 21, 2014. ClinicalTrials.gov Identifier: NCT02070757 (Study not yet open for participant recruitment).
U.S. National Institutes of Health, 'Safety and Efficacy Study of IV CXA-101 and IV Ceftazidime in Patients with Complicated Urinary Tract Infections'. Sponsored by Cubist Pharmaceuticals. http://www.clinicaltrials.gov/ct2/show/NCT00921024?term=ceftolozane &rank=4 Updated Aug. 5, 2010. ClinicalTrials.gov Identifier: NCT00921024 (Study has been completed).
U.S. National Institutes of Health, 'Safety and Efficacy Study to Compare IV CXA 101/Tazobactam and Metronidazole With Meropenem in Complicated Intraabdominal Infections'. Sponsored by Cubist Pharmaceuticals. http://www.clinicaltrials.gov/ct2/show/NCT01147640?term=ceftolozane&rank=2 Updated May 5, 2011. ClinicalTrials.gov Identifier: NCT01147640 (Study has been completed).
U.S. National Institutes of Health, 'Study of Intravenous Ceftolozane/Tazobactam vs. Piperacillin/Tazobactam in Ventilator Associated Pneumonia'. Sponsored by Cubist Pharmaceuticals. http://www.clinicaltrials.gov/ct2/show/NCT01853982?term=ceftolozane&rank=3 Updated Jan. 28, 2014. ClinicalTrials.gov Identifier: NCT01853982 (Study has been terminated).
Wootton et al: BAL 9141, a new borad-spectrum pyrrolidinone cephalosporin: activity against clinically significant anaerobes in comparison with 10 other antimicrobials; Journal of Antimicrobial Chemotherapy; (2002) vol. 49, pp. 535-539.
Written Opinion of the International Searching Authority for PCT/US2012/054191, dated Feb. 20, 2013, 7 pages.
Yoshizawa: New broad-spectrun parenteral cephalosporins exhibiting potent activity against both methicilln-resistant *Staphlococcus aureus* (MRSA) and Pseudomonas aeruginosa. Part 3: &Beta-[2-(5-Amino-1,2,4-thiadiazol-3-yl)-2-ethoxtiminoacetamido] cephalosporins bearing 4[3-(aminoalkyl)-ureido]-1-pyridinium at C3; Bioorg. Med. Chem. Lett.; 2004, vol. 12, pp. 4221-4231.
Ambrose, et al: Pharmacokinetic-pharmacodynamic considerations in the design of hospital-acquired or ventilator-associated bacterial pneumonia studies: look before you leap!; Clin Infect Dis, 2010, vol. 51, Suppl 1, pp. S103-S110.
American Thoracic Society; Infectious Diseases Society of America; Guidelines for the management of adults with hospital-acquired, ventilator-associated, and healthcare-associated pneumonia; Am J Respir Crit Care Med., 2005, vol. 171(4), pp. 388-416.
Baughman, et al: The diagnosis and treatment challenges in nosocomial pneumonia; Diagn Microbiol Infect Dis, vol. 33(2), pp. 131-139.
Bergogne-Berezin: Predicting the efficacy of antimicrobial agents in respiratory infections: is tissue concentration valid measure?; J Antimicrob Chemother, 1995, vol. 35, pp. 363-371.
Boselli, et al: Steady-state plasma and intrapulmonary concentrations of piperacillin/tazobactam 4 g10.5 g administered to critically ill patients with severe nosocomial pneumonia; Intensive Care Med, 2004, vol. 30, pp. 976-979.
Boselli, et al: Alveolar concentrations of piperacillin/tazobactam administered in continuous infusion to patients with—associated pneumonia; Crit Care Med, 2008, vol. 36, pp. 1500-1506.
Chastre, et al: Ventilator-associated pneumonia; Am J Respir Crit Care Med, 2002, vol. 165(7), pp. 867-903.
Chastre, et al: Comparison of 8 vs 15 days of antibiotic therapy for ventilator-associated pneumonia in adults: a randomized trial; JAMA, 2003, vol. 290(19), pp. 2588-2598.
El Solh: Update on the treatment of Pseudomonas aeruginosa pneumonia; J Antimicrob Chemother, 2009, vol. 64, pp. 229-238.
Freire, et al: Comparison of tigecycline with imipenem/cilastatin for the treatment of hospital-acquired penumonia; Diag Microbio and Infec Dis, 2010, vol. 68, pp. 140-151.
Harrison's Principles of Internal Medicine: Hospital-Acquired (Nosocomial) Pneumonia; ed. Kasper, et al.; 16th ed. New York: McGraw-Hill, Medical Pub. Division. 2005, pp. 1538-1541.
Jones, et al: Microbial etiologies of hospital-acquired bacterial pneumonia and ventilator-associated bacterial pneumonia; Clin Infect Dis; 2010, Suppl 1, pp. S81-S87.
Joseph, et al: Ventilator-associated pneumonia: A Review; EurJ Intern Med; 2010, vol. 21(5), pp. 360-368.
Klevens, et al: Estimating health care-associated infections and deaths in U.S. hospitals, 2002; Public Health Rep, 2007, vol. 122, pp. 160-166.
Knaus, et al: Apache II: A severity of disease classification system; Crit Care Med, 1985, vol. 13, pp. 818-829.
Komuro, et al: Inhibition of the renal excretion of tazobactam by piperacillin; J Antimicrob Chemother, 1994, vol. 34, pp. 555-564.
Lucasti: A Phase 3, Randomized, Double-Blind Study of Ceftobiprole Medocaril Versus Linezolid Plus Ceftazidime in the Treatment of Nosocomial Pneumonia; Ceftobiprole: Clinical Study Report Synopsis BAP00248/307; Issue Date: Jul. 14, 2010; Document No. EDMS-PSDB-6906024:3.0, (8 pages).
Mesaros, et al: Pseudomonas aeruginosa: resistance and therapeutic options at the turn of the new millennium; Clin Microbiol Infect, 2007, vol. 13, pp. 560-578.
Occhipinti, et al: Pharmacokinetics and pharmacodynamics of two multiple-dose piperacillin-tazobactam regimens; Antimicrob Agents Chemother, 1997, vol. 41, pp. 2511-2517.
Pankey: Tigecycline; J Antimicrob Chemotherapy, 2005, vol. 56, pp. 470-480.
Pea: The antimicrobial therapy puzzle: could pharmacokinetic-pharmacodynamic relationships be helpful in addressing the issue of appropriate pneumonia treatment in critically ill patients?; Clin Infect Dis, 2006, vol. 42, pp. 1764-1771.

(56) References Cited

OTHER PUBLICATIONS

Richards, et al: Nosocomial infections in medical intensive care units in the United States. National Nosocomial Infections Surveillance System; Crit Care Med, 1999, Vol.27(5), pp. 887-892.
Schulgen, et al: Estimation of extra hospital stay attributable to nosocomial infections: heterogeneity and timing of events; J Clin Epidemiol; Apr. 2000, vol. 53(4), pp. 409-417.
Singh:et al: Short-course empiric antibiotic therapy for patients with pulmonary infiltrates in the intensive care unit. A proposed solution for indiscriminate antibiotic prescription; Am J Respir Crit Care Med, Aug. 2000, vol. 162(2, Pt 1), pp. 505-511.
Udy, et al: Augmented renal clearance: implications for antibacterial dosing in the critically ill; Clin Pharmacokinet, 2010, vol. 49(1), pp. 1-16.
Vincent, et al: Use of the SOFA score to assess the incidence of organ dysfunction/failure in intensive care units: results of a multicenter, prospective study. Working group on "sepsis-related problems" of the European Society of Intensive Care Medicine; Crit Care Med, 1998, vol. 26(11), pp. 1793-1800.
Wunderink, et al: Linezolid in methicillin-resistant *Staphylococcus aureus* nosocomial pneumonia: a randomized, controlled study; Clin Infect Dis, 2012, vol. 54(5), pp. 621-629.
Zilberberg, et al: Epidemiology of healthcare-associated pneumonia (HCAP); Semin Respir Crit Care Med, 2009, vol. 30, pp. 10-15.
Zosyn®. Prescribing Information. Wyeth Pharmaceuticals, Inc., Philadelphia, PA, USA; http://labeling.pfizer.com/showlabeling.aspx?id=416 (Apr. 23, 2012, date last accessed), 26 pages.
Arin et al, 'The Comparative Stability of Different Types of Penicillin and Cephalosporin N-pyrryl derivatives'. Pharmazie 1988, vol. 43, pp. 18-19.
Cefazolin, (For Injection USP) Approved Dec. 1988, Product Label, B. Braun Medical Inc. Revised Jan. 2012.
Ceftazidime, (Systemic) Approved Nov. 1985, Product Label. American Society of Health-System Pharmacists Inc. 2004.
Claforan, (Sterile—Cefotaxime for injection, USP & Injection—Cefotaxime injection) Approved Prior to Jan. 1982, Product Label. Sanofi-Aventis U.S. LLC 2011.
Cubist Pharmaceuticals, 'Cubist Announces Positive Results from Two Phase 2 Trials, CXA-201 and CDAD Program'. Cubist Press Release. Jun. 2011.
Doribax, Approved Oct. 2007, Product Label. Ortho-McNeil-Janssen Pharmaceuticals, Inc. 2007.
Fortaz, (ceftazidime for Injection) (Ceftazidime Injection) Approved Jul. 1985, Product Label. GlaxoSmithKline 2007.
Maxipime, (Cefepime Hydrochloride, USP) Approved Jan. 1996, Product Label. Bristol-Myers Squibb Company, Revised Mar. 2009.
Yamana et al, 'Comparative Stability of Cephalosporins in Aqueous Solution: Kinetics and Mechanisms of Degradation'. Journal of Pharmaceutical Sciences 1976, vol. 65, No. 11, pp. 1563-1574.
Rocephin, (Ceftiaxone Sodium) Approved Aug. 1993, Product Label. Roche Laboratories, Copyright 1998.
Zithromax, (azithromycin injection) Approved Sep. 1994, Product Label. Pfizer Labs, Revised Feb. 2013.
Teflaro, (Ceftaroline fosamil) Approved Oct. 2010, Product Label. Forst Laboratories, Inc. 2010.
Non-Final Office Action issued for U.S. Appl. No. 14/214,212. Dated May 16, 2014, 11 pages.
Notice of Allowance issued for U.S. Appl. No. 14/214,212. Dated Aug. 4, 2014, 6 pages.
Notice of Abandonment issued for U.S. Appl. No. 14/214,212. Dated Nov. 19, 2014, 1 page.
Non-Final Office Action issued for U.S. Appl. No. 14/285,185. Dated Jul. 25, 2014, 9 pages.
Notice of Allowance issued for U.S. Appl. No. 14/285,185. Dated Dec. 16, 2014, 6 pages.
Non-Final Office Action issued for U.S. Appl. No. 14/251,372. Dated Sep. 5, 2014, 19 pages.
Notice of Allowance issued for U.S. Appl. No. 14/251,372. Dated Jan. 2, 2015, 5 pages.
Non-final Office Action issued for U.S. Appl. No. 14/212,781. Dated Mar. 2, 2015, 36 pages.
Non-final Office Action issued for U.S. Appl. No. 14/214,417. Dated Feb. 23, 2015, 12 pages.
Non-final Office Action issued for U.S. Appl. No. 14/522,893. Dated Feb. 9, 2015, 12 pages.
Non-final Office Action issued for U.S. Appl. No. 14/251,381. Dated Mar. 11, 2015, 16 pages.
Non Final Office Action issued for U.S. Appl. No. 14/212,625. Dated Apr. 9, 2015, 15 pages.
Non Final Office Action issued for U.S. Appl. No. 14/213,532. Dated Apr. 21, 2015, 18 pages.
Requirement for Restriction/Election issued for U.S. Appl. No. 14/212,625. Dated Jan. 23, 2015, 6 pages.
Requirement for Restriction/Election issued for U.S. Appl. No. 14/212,781. Dated Jun. 13, 2014, 6 pages.
Requirement for Restriction/Election issued for U.S. Appl. No. 14/214,367. Dated Dec. 16, 2014, 9 pages.
Requirement for Restriction/Election issued for U.S. Appl. No. 14/213,997. Dated Feb. 6, 2015, 6 pages.
Requirement for Restriction/Election issued for U.S. Appl. No. 14/214,260. Dated Feb. 12, 2015, 5 pages.
Cubist Pharmaceuticals (Business Wire. Cubist Pharmaceuticals Announces Approval of Second Bulk Drug Manufacturing Facility. 2005).
FDA CGMP Guidance (Guidance for Industry: Non-Penicillin Beta-Lactam Drugs: A CGMP Framework for preventing Cross Contamination. FDA. Apr. 2013.1-10).
FDA Compliance Policy Guides, "CPG Sec 430.100 Unit Dose Labeling for Solid and Liquid Oral Dosage Forms," Jun. 7, 2011. Online [http://web.archive.org/web/2011 0607033315 /http://www.fda.gov/ICECI/ ComplianceManuals/ CompliancePolicyGuidanceManual/ucm074377.htm].
Shanley, Agnes. (2013) Pharmaceutical Manufacturing. Facilities of the Future. <http://www.pharmamanufacturing.com/articles/2013/011/>.
Abstract for Sader et al. 'Antimicrobial Activity of Ceftolozane/Tazobactam Tested Against Gram-negative Bacterial Isolates from Hospitalized Patients with Pneumonia in United States (USA) and European (EU) Hospitals (2012)'. 53rd Annual Interscience Conference on Antimicrobial Agents and Chemotherapy (ICAAC 2013); Sep. 10-13, 2013; Denver, CO. Poster C2-1633.
Abstract for Sader et al. 'Post Beta-Lactamase Inhibitor Effect of Tazobactam When Associated with Ceftolozane and Tested against ESBL-Producing Strains'. 53rd Annual Interscience Conference on Antimicrobial Agents and Chemotherapy (ICAAC 2013); Sep. 10-13, 2013; Denver, CO. Poster A-1030.
Abstract for Vanscoy et al. 'Relationship between Ceftolozane/Tazobactam (TOL/TAZ) Exposure and *E. coli* Resistance Amplification Prevention in a Hollow Fiber Infection Model (HFIM)'. 53rd Annual Interscience Conference on Antimicrobial Agents and Chemotherapy (ICAAC 2013); Sep. 10-13, 2013; Denver, CO. Poster A-1031.
Abstract for Vanscoy et al. 'Identification of a Translational Relationship Between Tazobactam (TAZ) Exposure in Combination with Ceftolozane (TOL) and Efficacy Against ESBL-Producing Enterobacteriaceae'. 53rd Annual Interscience Conference on Antimicrobial Agents and Chemotherapy (ICAAC 2013); Sep. 10-13, 2013; Denver, CO. Poster A-1032.
Abstract for Zhanel et al. 'In Vitro Activity of Ceftolozane/Tazobactam Against 5,715 Gram-Negative and Gram-Positive Pathogens Isolated from Patients in Canadian Hospitals in 2011 and 2012: Canward Surveillance Study'. 53rd Annual Interscience Conference on Antimicrobial Agents and Chemotherapy (ICAAC 2013); Sep. 10-13, 2013; Denver, CO. Poster E-1689.
Abstract for Zilberberg et al. 'Multidrug resistant Pseudomonas aeruginosa among hospitalized patients with pneumonia, US 2000-2009'. Making a Difference in Infectious Diseases Pharmacotherapy Conference (MAD-ID 2013); May 9-11, 2013; Orlando, FL. Encore Presentation from ISICEM 2013.
Abstract for Zilberberg et al. 'Gram-negative resistance and need for ICU among urinary tract infections in the US'. Making a Difference

(56) References Cited

OTHER PUBLICATIONS in Infectious Diseases Pharmacotherapy Conference (MAD-ID 2013); May 9-11, 2013; Orlando, FL. Encore Presentation from ISICEM 2013.

Abstract for Zilberberg et al. 'Multidrug resistance among P. aeruginosa and Enterobacteriaceae in the US hospitals, 2000-2009'. Making a Difference in Infectious Diseases Pharmacotherapy Conference (MAD-ID 2013); May 9-11, 2013; Orlando, FL. Encore Presentation from SCCM 2013.

Abstract for Chandorkar et al. 'Target Attainment Rates (TAR) and Cumulative Fraction of Response (CFR) in Plasma for Ceftolozane in a Simulated Population of Patients with Complicated Intra-abdominal (cIAI) and Urinary Tract Infection (cUTI)'. 23rd Annual Meeting of the European Congress of Clinical Microbiology (ECCMID 2013); Apr. 27-30, 2013; Berlin, Germany. Poster P2742.

Abstract for Halimi et al. 'Comparative Evaluation of Ceftolozane/tazobactam MIC testing with Etest® and CLSI Broth Microdilution Methods'. 23rd Annual Meeting of the European Congress of Clinical Microbiology (ECCMID 2013); Apr. 27-30, 2013; Berlin, Germany. Poster P1606.

Abstract for Reynolds et al. 'Pseudomonas aeruginosa in the UK and Ireland: Susceptibility to Old and New Agents'. 23rd Annual Meeting of the European Congress of Clinical Microbiology (ECCMID 2013); Apr. 27-30, 2013; Berlin, Germany. Poster P1519.

Abstract for Sader et al. 'Antimicrobial activity of ceftolozane/tazobactam and comparator agents tested against Pseudomonas aeruginosa strains from 14 European countries and Israel'. 23rd Annual Meeting of the European Congress of Clinical Microbiology (ECCMID 2013); Apr. 27-30, 2013; Berlin, Germany. Poster P337.

Abstract for Noel et al. 'Pharmacodynamics of Ceftolozane/Tazobactam Against Gram Negative Bacilli'. 53rd Annual Interscience Conference on Antimicrobial Agents and Chemotherapy (ICAAC 2013); Sep. 10-13, 2013; Denver, CO. Poster.

Abstract for Melchers et al. 'Pharmacokinetics of Tazobactam and Ceftolozane Alone and in Combination in Mice'. 53rd Annual Interscience Conference on Antimicrobial Agents and Chemotherapy (ICAAC 2013); Sep. 10-13, 2013; Denver, CO. Poster A-1033.

Abstract for Melchers et al. 'Pharmacodynamics of Ceftolozane Combined with Tazobactam in a Neutropenic Mouse Thigh Model'. 53rd Annual Interscience Conference on Antimicrobial Agents and Chemotherapy (ICAAC 2013); Sep. 10-13, 2013; Denver, CO. Poster A-1034.

Abstract for Lucasti et al. 'A Multicenter, Double-Blind, Randomized, Phase 2 Study to Assess the Safety and Efficacy of Ceftolozane/Tazobactam (TOL/TAZ) plus Metronidazole (MTZ) Compared to Meropenem (MER) in Adult Patients with Complicated Intra-abdominal Infections (cIAI)'. 53rd Annual Interscience Conference on Antimicrobial Agents and Chemotherapy (ICAAC 2013); Sep. 10-13, 2013; Denver, CO. Poster K-1709.

Abstract for Estabrook et al. 'In vitro Activity of CXA-201 (Ceftolozane-Tazobactam) Against 200 CTX M-Producing *Escherichia coli* Clinical Isolates'. 53rd Annual Interscience Conference on Antimicrobial Agents and Chemotherapy (ICAAC 2013); Sep. 10-13, 2013; Denver, CO. Poster E-1169.

Abstract for Bulik et al. 'In vitro activity of CXA-101, a novel cephalosporin, against resistant phenotypes of Pseudomonas aeruginosa'. 47th Annual Meeting of the Infectious Diseases Society (IDSA 2009); Oct. 29-Nov. 1, 2009; Philadelphia, PA. Poster 209.

Abstract for Moya et al. 'Activity of CXA-101 against Pseudomonas aeruginosa beta-lactam resistance mechanisms: ampD, ampDh2, ampDh2, dacB, and oprD mutations'. 49th Annual Interscience Conference on Antimicrobial Agents and Chemotherapy (ICAAC 2009); Sep. 12-15, 2009; San Francisco, CA. Poster F1-1989.

Abstract for Livermore et al. 'Chequerboard titrations of cephalosporin CXA-101 and tazobactam vs. beta-lactamase producing Enterobacteriaceae'. 49th Annual Interscience Conference on Antimicrobial Agents and Chemotherapy (ICAAC 2009); Sep. 12-15, 2009; San Francisco, CA. Poster F1-1994.

Abstract for Jacqueline et al. 'ED50 Determination of CXA-101 Alone and in Combination with Tazobactam for Treating Experimental Peritonitis in Mice Due to ESBL-Producing Klebsiella pneumoniae strains: Comparison with Ceftazidime and Piperacillin/Tazobactam'. 50th Annual Interscience Conference on Antimicrobial Agents and Chemotherapy (ICAAC 2010); Sep. 12-15, 2010; Boston, MA. Poster B-708.

Abstract for Cabot et al. 'Pseudomonas aeruginosa Ceftolozane/Tazobactam Resistance Development Requires Multiple Mutations Leading to Overexpression and Structural Modification of AmpC'. 53rd Annual Interscience Conference on Antimicrobial Agents and Chemotherapy (ICAAC 2013); Sep. 10-13, 2013; Denver, CO. Poster C1-060.

Abstract for Jacqueline. 'In vivo Activity of CXA-101 against Pseudomonas aeruginosa in a Rabbit Experimental Pneumonia: Comparison with Ceftazidime Piperacillin-Tazobactam and Imipenem'. 51st Annual Interscience Conference on Antimicrobial Agents and Chemotherapy (ICAAC 2011); Sep. 17-20, 2011; Chicago, IL. Poster B-590.

Abstract for Reynolds et al. 'Enterobacteriaceae in the UK and Ireland: Susceptibility to Old and New Agents'. 52nd Annual Interscience Conference on Antimicrobial Agents and Chemotherapy (ICAAC 2012); Sep. 9 12, 2012; San Francisco, CA. Poster C2-152.

Abstract for Miller et al. 'Safety and Pharmacokinetics of Intravenous Ceftolozane/tazobactam 3 g every 8 Hours and Cumulative Fraction of Response in Plasma and Epithelial Lining Fluid in a Simulated Ventilator Associated Pneumonia Population'. 52nd Annual Interscience Conference on Antimicrobial Agents and Chemotherapy (ICAAC 2012); Sep. 9-12, 2012; San Francisco, CA. Poster A-624.

Abstract for Melchers et al. 'In vitro Activity of CXA-101 Alone and In Combination With Tazobactam Against Extended Spectrum Beta-lactamase Harbouring Enterobacteriaceae'. 52nd Annual Interscience Conference on Antimicrobial Agents and Chemotherapy (ICAAC 2012); Sep. 9-12, 2012; San Francisco, CA. Poster E 198.

Abstract for Zilberberg et al. 'Prevalence of beta-lactam resistance among P. aeruginosa in US hospitals, 2000-2009'. To be presented at the 2nd Annual IDWeek (IDWeek 2013); Oct. 2-6, 2013; San Francisco, CA. Poster #1580.

Abstract for Cabot et al. 'Dynamics and mechanisms of resistance development to ceftazidime, meropenem and ceftolozane-/tazobactam in wild-type and mutator P. aeruginosa strains'. 52nd Annual Interscience Conference on Antimicrobial Agents and Chemotherapy (ICAAC 2012); Sep. 9-12, 2012; San Francisco, CA. Poster C1-1970.

Abstract for Sader et al. 'Frequency of occurrence and antimicrobial susceptibility of Gram-negative organisms isolated from health care associated urinary tract infections: Results from the Program to Assess Ceftolozane/Tazobactam Susceptibility (Pacts)'. To be presented at the 2nd Annual IDWeek (IDWeek 2013); Oct. 2-6, 2013; San Francisco, CA. Poster.

Abstract for Zilberberg et al. 'Secular trends in gram-negative resistance among urinary tract infection hospitalizations in the US, 2000-2009'. 23rd Annual Meeting of the European Congress of Clinical Microbiology (ECCMID 2013); Apr. 27-30, 2013; Berlin, Germany. Poster P1517.

Abstract for Vanscoy et al. 'Pharmacokinetics-Pharmacodynamics (PK-PD) of Tazobactam in Combination with Ceftolozane in an In Vitro Infection Model'. 23rd Annual Meeting of the European Congress of Clinical Microbiology (ECCMID 2013); Apr. 27-30, 2013; Berlin, Germany. Poster P900.

Abstract for Sader et al. 'Ceftolozane/tazobactam activity tested against aerobic Gram-negative organisms isolated from intraabdominal infections in European and United States hospitals (2012)'. To be presented at the 2nd Annual IDWeek (IDWeek 2013); Oct. 2-6, 2013; San Francisco, CA. Poster #698.

Abstract for Sader et al. 'Antimicrobial susceptibility of gram-negative bacteria causing urinary tract infections in European and United States hospitals (2009-2011)'. 23rd Annual Meeting of the European Congress of Clinical Microbiology (ECCMID 2013); Apr. 27-30, 2013; Berlin, Germany. Poster P1516.

Abstract for Chandorkar et al. 'Population Pharmacokinetics (PPK) Meta-Analysis of Ceftolozane/Tazobactam in Healthy Volunteers

(56) References Cited

OTHER PUBLICATIONS and Patients'. Presented at the Annual Meeting of the American College of Clinical Pharmacy (ACCP 2013); Oct. 13-16, 2013; Albuquerque, NM. Poster # 120.
Abstract for Chandorkar et al. 'Pharmacokinetics and Safety of Ceftolozane/Tazobactam in Subjects with Severe Renal Impairment or End Stage Renal Disease on Hemodialysis'. To be presented at the 2nd Annual IDWeek (IDWeek 2013); Oct. 2-6, 2013; San Francisco, CA. Poster #723.
Abstract for Sader et al. 'Antimicrobial activity of ceftolozane/tazobactam and comparator agents tested against Pseudomonas aeruginosa isolates from United States (USA) medical centers (2011-2012)'. To be presented at the 2nd Annual IDWeek (IDWeek 2013); Oct. 2-6, 2013; San Francisco, CA. Poster #695.
Wooley et al. 'Impact of renal function on the pharmacokinetics and safety of ceftolozane-tazobactam'. Antimicrob Agents Chemother. 2014 vol. 58, No. 4, pp. 2249-2255.
Sader et al. 'Post-β-Lactamase-Inhibitor Effect of Tazobactam in Combination with Ceftolozane on ExtendedβSpectrum-β-Lactamase-Producing Strains'. Antimicrob Agents Chemother. 2014 vol. 58 No. 4, pp. 2434-243.
Cabot et al. 'Pseudomonas aeruginosa Ceftolozane-Tazobactam Resistance Development Requires Multiple Mutations Leading to Overexpression and Structural Modification of AmpC'. Antimicrob Agents Chemother. Mar. 17, 2014. [Epub ahead of print] PubMed PMID: 24637685.
Snydman et al. 'Activity of Ceftolozane/Tazobactam Against a Broad Spectrum of Recent Clinical Anaerobic Isolates'. Antimicrob Agents Chemother. 2014 vol. 58, No. 2, pp. 1218-1223.
Zhanel et al. 'Ceftolozane/Tazobactam: A Novel Cephalosporin/β-Lactamase Inhibitor Combination with Activity Against Multidrug-Resistant Gram-Negative Bacilli'. Drugs. 2014 vol. 74 No. 1, pp. 31-51.
Vanscoy et al. 'Pharmacological basis of β-lactamase inhibitor therapeutics: tazobactam in combination with Ceftolozane'. Antimicrob Agents Chemother. 2013. vol. 57 No. 12, pp. 5924-5930.
Toda et al. 'FR264205, A Novel Parenteral Antipseudomonal Cephem: Synthesis and SAR of 3-(2,4-Disubstituted 3-Aminopyrazolio)methyl Cephalosporins'. 46th Annual Interscience Conference on Antimicrobial Agents and Chemotherapy (ICAAC 2006); Sep. 27-30, 2006; San Francisco, CA. Oral Presentation F1-0240.
Walkty et al. 'In vitro activity of ceftolozane-tazobactam against Pseudomonas aeruginosa isolates obtained from patients in Canadian hospitals in the CANWARD study, 2007 to 2012'. Antimicrob Agents Chemother. 2013, vol. 57, No. 11, pp. 5707-5709.
Hong et al. 'Ceftolozane/tazobactam: a novel antipseudomonal cephalosporin and β-lactamase-inhibitor combination'. Infect Drug Resist. 2013 vol. 29, No. 6, pp. 215-223.
Zilberberg et al. 'Prevalence of multidrug-resistant Pseudomonas aeruginosa and carbapenem-resistant Enterobacteriaceae among specimens from hospitalized patients with pneumonia and bloodstream infections in the United States from 2000 to 2009'. J Hosp Med. 2013 vol. 8, No. 10, pp. 559-563.
Zilberberg et al. 'Secular Trends in Gram-Negative Resistance among Urinary Tract Infection Hospitalizations in the United States, 2000-2009'. Infect Control Hosp Epidemiol. 2013, vol. 34, No. 9, pp. 940-946.
Hayakawa et al. 'Epidemiology and Risk Factors for Isolation of *Escherichia coli* Producing CTX-M-Type Extended-Spectrum β-Lactamase in a Large U.S. Medical Center'. Antimicrob Agents Chemother. 2013 vol. 57, No. 8, pp. 4010-8.
Vanscoy et al. 'Relationship between Ceftolozane/Tazobactam Exposure and Drug-Resistance Amplification in a Hollow-Fiber Infection Model'. Antimicrob Agents Chemother. Jun. 17, 2013. [Epub ahead of print] PubMed PMID: 23774429.
Vanscoy et al. 'Pharmacokinetics-Pharmacodynamics of Tazobactam in Combination with Ceftolozane in an In Vitro Infection Model'. Antimicrob Agents Chemother. 2013 vol. 57, No. 6, pp. 2809-2814.

Craig et al. 'In-Vivo Activity of Ceftolozane, a New Cephalosporin, with and without Tazobactam against Pseudomonas aeruginosa and Enterobacteriaceae, including Strains with Extended-Spectrum β-Lactamases, in the Thighs of Neutropenic Mice'. Antimicrob Agents Chemother. 2013 vol. 57, No. 4, pp. 1577-1582.
Jacqueline et al. 'Efficacy of ceftolozane in a murine model of Pseudomonas aeruginosa acute pneumonia: in vivo antimicrobial activity and impact on host inflammatory response'. J Antimicrob Chemother. 2013 vol. 63, No. 1, pp. 177-83.
Miller et al. 'CXA-201 dose selection based on probability of target attainment and drug exposure in subjects with varying degrees of renal impairment'. 51st Annual Interscience Conference on Antimicrobial Agents and Chemotherapy (ICAAC 2011); Sep. 17-20, 2011; Chicago, IL. Oral Presentation A-1099.
Titelman et al. 'In vitro activity of CXA-101 plus tazobactam against CTX-M-14- and CTX-M-15-producing *Escherichia coli* and *Klebsiella pneumoniae*'. Diagn Microbiol Infect Dis. 2011 vol. 70, No. 1, pp. 137-141.
Ge et al. 'Pharmacokinetics and safety of CXA-101, a new antipseudomonal cephalosporin, in healthy adult male and female subjects receiving single- and multiple-dose intravenous infusions'. Antimicrob Agents Chemother. 2010 vol. 54, No. 8, pp. 3427-3431.
Juan et al. 'Activity of a new antipseudomonal cephalosporin, CXA-101, against carbapenem-resistant and multidrug-resistant Pseudomonas aeruginosa clinical strains'. Antimicrob Agents Chemother. 2010, vol. 54, No. 2, pp. 846-851.
Sader et al. 'Antimicrobial Activity of Ceftolozane/Tazobactam Tested Against Gram-Negative Bacterial Isolates from Hospitalized Patients with Pneumonia in European Hospitals (2011)'. 23rd Annual Meeting of the European Congress of Clinical Microbiology (ECCMID 2013); Apr. 27-30, 2013; Berlin, Germany. Oral Presentation O-181.
Nicasio et al. 'PK-PD of Tazobactam (TAZ) in Combination with Piperacillin (PIP) in an In Vitro Infection Model (IVIM)'. 53rd Annual Interscience Conference on Antimicrobial Agents and Chemotherapy (ICAAC 2013); Sep. 10-13, 2013; Denver, CO. Oral Presentation.
Non-Final Office Action issued for U.S. Appl. No. 14/214,234, mailed Jul. 7, 2014 (16 pages).
U.S. Appl. No. 14/285,185, filed Apr. 11, 2014. 77 pages.
Miller et al. 'Pharmacokinetics and Safety of Intravenous Ceftolozane-Tazobactum in Healthy Adult Subjects following Single and Multiple Ascending Doses'. Antimicrobial Agents and Chemotherapy. 2012. vol. 56, No. 6, pp. 3086-3091.
Office Action issued for U.S. Appl. No. 14/250,879. Dated Jul. 8, 2014. 40 pages.
Lehr et al. 'Particulate Matter Contamination of Intravenous Antibiotics Aggravates Loss of Functional Capillary Density in Postischemic Striated Muscle'. Am. J. Respir. Crit. Care Med. 2002, vol. 165, pp. 514-520.
Alexov et al. Efficacy of Ampicillin-Sulbactam Is not Dependent upon Maintenance of a Critical Ratio between Components: Sulbactam Pharmacokinetics in Pharmacodynamic Interactions. Antimcirobial Agents Chemotherapy 1996;40:2468.
Bush et al. Kinetic Interactions of Tazobactam with Beta-Lactamases from All Major Structural Classes. Antimicrobial Agents and Chemotherapy 1993;37:851.
Hatano et al. In vivo Anti-Pseudomonas Aeruginosa Activity of Novel Parenteral Cephalosporin, FR264205. 45th Annual Interscience Conference on Antimicrobial Agents and Chemotherapy (ICAAC 2005); Dec. 16-19, 2005. Oral Presentation F-1165.
Kurpiel. Point Mutations in the Inc Antisense RNA Gene Are Associated with Increased Plasmid Copy Number, Expression of BlaCMY-2 and Resistance to Piperacillin/Tazobactam in *Escherichia Coli*. Journal of Antimicrobial Chemotherapy 2012;67:339.
Lister et al. Importance of Beta-Lactamase Inhibitor Pharmacokinetics in the Pharmacodynamics of Inhibitor-Drug Combinations: Studies with Piperacillin-Tazobactam and Piperacillin-sulbactam. Antimicrobial Agents and Chemotherapy 1997;41:721.

(56) References Cited

OTHER PUBLICATIONS

Louie et al., Pharmacodynamics of b-Lactamase Inhibition by NXL104 in Combination with Cefaroline: Examining Organisms with Multiple Types of b-Lacramases. Antimicrobial Agents and Chemotherapy. 2012, 56, 258.
Miller et al. CXA-201 dose selection based on probability of target attainment and drug exposure in subjects with varying degrees of renal impairment. ICAAC 2011. Oral Presentation A-1099.
Seetulsingh et al. Activity of Clavulanate Combinations against TEM-1 b-Lactamase-Producing *Escherichia coli* Isolates Obtained in 1982 and 1989. Journal of Antimicrobial Chemotherapy 1991;27:749.
Soon et al. A Novel Mathematical Modeling Approach to Characterize the Pharmacodynamics of Ceftolozane/Tazobactam, a β-lactam & β-lactannase Inhibitor Combination. 52nd Annual Interscience Conference on Antimicrobial and Chemotherapy (ICAAC 2012); Sep. 9-12, 2012. Oral Presentation A-1762.
Steenbergen et al. Potency of CXA-101Tazobactam for Pathogens from ICU and non-ICU Correlated to Probability of Pharmacokinetic/Pharmacodynamic (PK/PD) Target Attainment. ICAAC 2011. Oral Presentation A-1689.
Strayer et al. Pharmacodynamics of Piperacillin Alone and in Combination with Tazobactam against Piperacillin-Resistant and -Susceptible Organisms in an In Vitro Model of Infection. Antimicrobial Agents and Chemotherapy 1994;38:2351.
Thomson et al. Beta-Lactamase Production in Memebers of the Family Enterobacteriaceae and Resistance to Beta-Lactam-Enzyme Inhibitor Combinations. Antimicrobial Agents and Chemotherapy 1990;34:622.
Bulik et al, In vivo comparison of CXA-101 with and without tazobactam versus piperacillin-tazobactam using human simulated exposures against phenotypically diverse gram-negative organisms. Antimicrob Agent Chemother 2012 56 (1):544-9.
Bulik et al., In vitro potency of CXA-101, a novel cephalosporin, against Pseudomonas aeruginosa displaying various resistance phenotypes, including multidrug resistance. Antimicrob Agents Chemother. 2010;54(1):557-9.
Chandorkar et al., Intrapulmonary penetration of ceftolozaneltazobactam and piperacillin/tazobactam in healthy adult subjects. J Antimicrob Chemother. 2012, 67, 2463.
Clinical and Laboratory Standards Institute CLSI Document M07-A9.
Clinical and Laboratory Standards Institute CLSI Document M100-S22.
Ge et al., Pharmacokinetics and safety of CXA-101, a new antipseudomonal cephalosporin, in healthy adult male and female subjects receiving single- and multiple-dose intravenous infusions. Antimicrob Agents Chemother. 2010 , 54: 3427-31.
Juan et al., Activity of a new antipseudomonal cephalosporin, CXA-101, against carbapenem-resistant and multidrugresistant Pseudomonas aeruginosa clinical strains. Antimicrob Agents Chemother. 2010;54(2):846-51.
Livermore et al., Chequerboard titration of cephalosporin CXA-101 and tazobactam versus beta-lactamase-producing Enterobacteriaceae. J Antimicrob Chemother. 2010 65 1972-4.
Miller et al., Pharmacokinetics and Safety of Intravenous Ceftolozane/tazobactam in Healthy Adult Subjects following Single and Multiple Ascending Doses. Antimicrob Agents Chemother. 2012 56:3086-91.
Moya et al., Activity of a new cephalosporin, CXA-101 (FR264205), against beta-lactam-resistant Pseudomonas aeruginosa mutants selected in vitro and after antipseudomonal treatment of intensive care unit patients. Antimicrob Agents Chemother. 2010 ;54(3):1213-7.
Moya et al., Affinity of the New Cephalosporin CXA-101 to Penicillin-Binding Proteins of Pseudomonas aeruginosa. Antimicrob Agents Chemother. 2010; 54: 3933-3937.
Moya et al., Pan-Beta-Lactam Resistance Development in Pseudomonas aeruginosa Clinical Strains: Molecular Mechanisms, Penicillin-Binding Protein Profiles, and Binding Affinities. Antimicrob Agents Chemother. 2012 56 4771-8.
Perletti et al., CXA-101—Cephalosporin Antibiotic. Drugs of the Future 2010; 35(12): 977-986.
Riera et al., Anti-biofilm and resistance suppression activities of CXA-101 against chronic respiratory infection phenotypes of Pseudomonas aeruginosa strain PAO1. J Antimicrob Chemother. 2010;65(7):1399-404.
Sader et al., Antimicrobial activity of CXA-101, a novel cephalosporin tested in combination with tazobactam against Enterobacteriaceae, Pseudomonas aeruginosa, and Bacteroides fragilis strains having various resistance phenotypes. Agents Chemother. 2011 55(5):2390-4.
Zamorano et al., Activity of the new cephalosporin CXA-101 against Pseudomonas aeruginosa isolates from chronically-infected cystic fibrosis patients. Clin Microbiol Infect. 2010 16(9):1482-7.
Clinical and Laboratory Standards Institute CLSI Document M100-S22; Jan. 2012, vol. 32, No. 3 (188 pages).
Extended European Search Report for Application No. 14160151.8, dated May 13, 2014, 9 pages.
Notification of Transmittal of the International Search Report and the Written Opinion of the International Searching Authority for International Application No. PCT/US2014/028642, Dated Aug. 7, 2014, 14 pages.
International Preliminary Report on Patentability corresponding to International Patent Application No. PCT/US2014/028642, issued Sep. 15, 2015.
Notice of Abandonment issued for U.S. Appl. No. 14/200,383, mailed Sep. 24, 2015.
Notice of Abandonment issued for U.S. Appl. No. 14/212,781, mailed Sep. 23, 2015.
Notice of Abandonment issued for U.S. Appl. No. 14/213,997, mailed Sep. 9, 2015.
Notice of Abandonment issued for U.S. Appl. No. 14/214,260, mailed Sep. 17, 2015.
Notice of Abandonment issued for U.S. Appl. No. 14/214,324, mailed Jan. 28, 2015.
Notice of Abandonment issued for U.S. Appl. No. 14/214,417, mailed Oct. 5, 2015.
Notice of Abandonment issued for U.S. Appl. No. 14/522,893, mailed Aug. 27, 2015.
Office Action issued for U.S. Appl. No. 14/200,383, mailed Mar. 2, 2015.
Office Action issued for U.S. Appl. No. 14/212,590, mailed Jun. 8, 2015.
Office Action issued for U.S. Appl. No. 14/214,324, mailed Jul. 7, 2014.
Office Action issued for U.S. Appl. No. 14/214,367, mailed Mar. 17, 2015.
Office Action issued for U.S. Appl. No. 14/250,879, mailed Mar. 16, 2015.
Office Action issued for U.S. Appl. No. 14/285,185, mailed Jul. 25, 2014.
Requirement for Restriction/Election issued for U.S. Appl. No. 14/228,401, mailed Mar. 30, 2015.
U.S. Appl. No. 14/250,879, filed Apr. 11, 2014.

* cited by examiner

Figure 3

Table 1

| Impurity | RRT |
|---|---|
| Peak 1 (P1) [1] | ~0.1 |
| Peak 2 (P2) | ~0.2 |
| Peak 3 (P3) | ~0.4 |
| Peak 4 (P4) | ~0.6 |
| Peak 5 (P5) | ~0.9 |
| CXA-101 [2] | 1.0 |
| Peak 6 (P6) | ~1.1 |
| Peak 7 (P7) | ~1.3 |
| Peak 8 (P8) | ~1.4 |
| Peak 9 (P9) | ~1.7 |
| Peaks 10, 11 (P10, 11) | ~2.3 |

1. The absolute retention time for Peak 1 is 3.5 minutes.
2. The absolute retention time for CXA-101 (ceftolozane) is 24 minutes.

Figure 4B

Table 2: Compositions of Co-lyophilization Drug Product.

| Component | Function | Amount (mg/vial) |
|---|---|---|
| CXA-101 | Active pharmaceutical ingredient | 1000 (potency) |
| L-arginine | Alkalization reagent | 587 |
| Citric acid (anhydrous) | Buffer | 21 |
| Sodium chloride | Stabilizer | 476 |
| Tazobactam (free acid) | Active pharmaceutical ingredient | 500 |
| Sodium bicarbonate | Alkalization reagent | Quantity sufficient[1] for pH 4.8 to 7.0 |
| water | Dissolution solvent | Not more than 4% by weight[2] |
| Nitrogen | Inert gas | Sufficient quantity |

1. Sodium content is approximately 78 mg/g of tazobactam in drug product after lyophilization.
2. Water is removed during the lyophilization process and is controlled at no more than 4% by weight.

Figure 5

Table 3: Formulation composition of the Co-Lyo Combo Drug Product.

| | | |
|---|---|---|
| CXA-201 Comp. | 16.3 g active | ceftolozane |
| | 8.1 g active | Tazobactam free ac. |
| | 15.5 g | L-Arginine |
| | 350 mg | Citric acid |
| | 7.9 g | NaCl |
| | 6.1 | pH compounded solution |

Figure 6A

Table 4

| Test items | Spec. D.P. | T0 | T1 25°C | T2 25°C |
|---|---|---|---|---|
| Related Substances | | | | |
| -Peak1 | ≤ 1.50% | 0.31% | 0.54% | 0.71% |
| -Peak2 | ≤ 0.40% | 0.07% | 0.07% | 0.09% |
| -Peak3 | ≤ 0.30% | <0.03% | <0.03% | <0.03% |
| -Peak4 | ≤ 0.80% | 0.08% | 0.08% | 0.09% |
| -Peak5 | ≤ 1.00% | 0.27% | 0.26% | 0.29% |
| -Peak6 | ≤ 0.15% | <0.03% | <0.03% | <0.03% |
| -Peak7 | ≤ 2.00% | 0.64% | 0.65% | 0.66% |
| -Peak8 | ≤ 0.15% | <0.03% | <0.03% | <0.03% |
| -Peak9 | ≤ 0.60% | 0.05% | 0.11% | 0.10% |
| -Peak10,11 | ≤ 0.15% each | 0.04% | 0.04% | 0.04% |
| -Peak12 | ≤ 2.00% | <0.03% | <0.03% | <0.03% |
| Others (RRT 0.43) | ≤ 0.15% | <0.03% | <0.03% | 0.04% |
| Others (RRT 1.22) | ≤ 0.15% | 0.13% | 0.30% | 0.38% |
| Others (RRT 2.18) | ≤ 0.15% | 0.03% | <0.03% | 0.05% |
| Others (RRT 2.77) | ≤ 0.15% | <0.03% | 0.03% | 0.03% |
| Sing. Unk. | ≤ 0.15% | 0.05% | 0.07% | 0.05% |
| Total | ≤ 5.00% | 1.67% | 2.19% | 2.77% |
| pH | report value | 5.5 | | 4.83 |

Figure 6B
Table 5

| Test items | Spec. D.P. | T0 | T1 40°C | T2 40°C |
|---|---|---|---|---|
| Related Substances | | | | |
| -Peak1 | ≤ 1.50% | 0.31% | 1.77% | 2.22% |
| -Peak2 | ≤ 0.40% | 0.07% | 0.10% | 0.16% |
| -Peak3 | ≤ 0.30% | <0.03% | <0.03% | 0.06% |
| -Peak4 | ≤ 0.80% | 0.08% | 0.09% | 0.09% |
| -Peak5 | ≤ 1.00% | 0.27% | 0.27% | 0.30% |
| -Peak6 | ≤ 0.15% | <0.03% | <0.03% | <0.03% |
| -Peak7 | ≤ 2.00% | 0.64% | 0.69% | 0.78% |
| -Peak8 | ≤ 0.15% | <0.03% | <0.03% | 0.10% |
| -Peak9 | ≤ 0.60% | 0.05% | 0.09% | 0.09% |
| -Peak10,11 | ≤ 0.15% each | 0.04% | 0.04% | 0.05% |
| -Peak12 | ≤ 2.00% | <0.03% | <0.03% | <0.03% |
| Others (RRT 0.43) | ≤ 0.15% | <0.03% | 0.09% | 0.15% |
| Others (RRT 1.22) | ≤ 0.15% | 0.13% | 0.74% | 0.97% |
| Others (RRT 2.18) | ≤ 0.15% | 0.03% | <0.03% | 0.08% |
| Others (RRT 2.77) | ≤ 0.15% | <0.03% | <0.03% | 0.04% |
| Sing. Unk. | ≤ 0.15% | 0.05% | 0.11% | 0.25% |
| Total | ≤ 5.00% | 1.67% | 4.49% | 6.32% |
| pH | report value | 5.5 | | 4.09 |

Figure 7

Table 6

| Test | Acceptance Limits (expected value) | Results | | | |
|---|---|---|---|---|---|
| | | Sampling | 60 minute | 120 minute | 180 minute |
| Content: Ceftolozane[1] | 30.4%-37.2% | 1 | 34.24 | 34.07 | 34.42 |
| | | 2 | 34.62 | 34.21 | 34.66 |
| | | 3 | 34.71 | 34.60 | 34.85 |
| | | Mean[3] | 34.52 | 34.30 | 34.64 |
| | | RSD% | 0.72 | 0.80 | 0.63 |
| Content: Tazobactam[2] | 15.2%-18.6% | 1 | 17.96 | 18.20 | 17.12 |
| | | 2 | 16.90 | 18.26 | 16.51 |
| | | 3 | 17.27 | 16.93 | 17.02 |
| | | Mean[3] | 17.38 | 17.80 | 16.89 |
| | | RSD% | 3.10 | 4.22 | 1.96 |
| Ratio of Content (w/w) ceftolozane/tazobactam | 2.00[4] | 1 | 1.91 | 1.87 | 2.01 |
| | | 2 | 2.05 | 1.87 | 2.10 |
| | | 3 | 2.01 | 2.04 | 2.05 |
| | | Mean[3] | 1.99 | 1.93 | 2.05 |
| | | RSD% | 3.69 | 5.12 | 2.2 |

RSD = relative standard deviation

[1] Theoretical value: 33.96% Acceptance limits are 90% - 110% of the theoretical value.

[2] Theoretical value: 16.99% Acceptance limits are 90% - 110% of the theoretical value.

[3] Three samples are taken at each time point at three places to measure the percentage by weight of ceftolozane and tazobactam. The "Mean" is the average of the percentages or the weight ratios of Ceftolozane/tazobactam.

[4] Acceptance limits were established based on batch history.

Figure 8

Table 7: Formulation composition of the blend Drug Product.

| | Component | Composition | Quantity as active components |
|---|---|---|---|
| CXA-201 Comp. | CXA-101 for Injection Bulk (25 g) | CXA-101 | 10.8 g |
| | | L-Arginine | 6.7 g |
| | | Citric acid | 233 mg |
| | | Sodium chloride | 5.2 g |
| | Tazobactam sodium sterile Bulk (6 g) | | 5.4 g (as Tazo free acid) |

Figure 9A

Table 8: Stability data of Blending Combo Drug Product at 25 °C/RH=60%.

| Test items | Specifications | T0 | T1 25°C | T2 25°C |
|---|---|---|---|---|
| Related Substances | | | | |
| -Peak1 | ≤ 1.50% | 0.61% | 0.93% | 1.08% |
| -Peak2 | ≤ 0.40% | <0.03% | <0.03% | <0.03% |
| -Peak3 | ≤ 0.30% | <0.03% | <0.03% | <0.03% |
| -Peak4 | ≤ 0.80% | 0.03% | 0.03% | 0.04% |
| -Peak5 | ≤ 1.00% | 0.09% | 0.12% | 0.13% |
| -Peak6 | ≤ 0.15% | <0.03% | <0.03% | <0.03% |
| -Peak7 | ≤ 2.00% | 1.28% | 1.34% | 1.35% |
| -Peak8 | ≤ 0.15% | <0.03% | <0.03% | <0.03% |
| -Peak9 | ≤ 0.60% | 0.03% | <0.03% | 0.03% |
| -Peak10,11 | ≤ 0.30% | <0.03% | 0.04% | 0.05% |
| Sing. Unk. | ≤ 0.15% | 0.13% | 0.13% | 0.14% |
| Total | ≤ 5.00% | 2.49% | 3.03% | 3.28% |
| Assay CXA-101 | Teor. %=32.6% | 32.5% | n.a. | n.a. |
| Assay Tazobactam | Teor. %=17.4% | 18.2% | n.a. | n.a. |
| Tazobactam Related Compound A | ≤ 4.0% | 0.07% | 0.12% | 0.14% |
| K.F. | ≤ 4.0% | 2.6% | n.a. | n.a. |
| pH | 5.0-7.0 | 6.0 | 5.6 | 5.1 |

Figure 9B

Table 9: Stability data of Blending Combo Drug Product at 40 °C/RH=75%.

| Test items | Specifications | T0 | T1 40°C | T2 40°C |
|---|---|---|---|---|
| Related Substances | | | | |
| -Peak1 | ≤ 1.50% | 0.61% | 1.66% | 2.28% |
| -Peak2 | ≤ 0.40% | <0.03% | <0.03% | <0.03% |
| -Peak3 | ≤ 0.30% | <0.03% | <0.03% | 0.04% |
| -Peak4 | ≤ 0.80% | 0.03% | 0.04% | 0.05% |
| -Peak5 | ≤ 1.00% | 0.09% | 0.13% | 0.14% |
| -Peak6 | ≤ 0.15% | <0.03% | <0.03% | <0.03% |
| -Peak7 | ≤ 2.00% | 1.28% | 1.41% | 1.46% |
| -Peak8 | ≤ 0.15% | <0.03% | <0.03% | <0.03% |
| -Peak9 | ≤ 0.60% | 0.03% | <0.03% | 0.03% |
| -Peak10,11 | ≤ 0.30% | <0.03% | 0.08% | 0.09% |
| Sing. Unk. | ≤ 0.15% | 0.13% | 0.14% | 0.13% |
| Total | ≤ 5.00% | 2.49% | 4.21% | 5.27% |
| Assay CXA-101 | Teor. %=32.6% | 32.5% | n.a. | n.a. |
| Assay Tazobactam | Teor. %=17.4% | 18.2% | n.a. | n.a |
| Tazobactam Related Compound A | ≤ 4.0% | 0.07% | 0.35% | 0.54% |
| K.F. | ≤ 4.0% | 2.6% | n.a. | n.a. |
| pH | 5.0-7.0 | 6.0 | 5.0 | 4.4 |

CEFTOLOZANE-TAZOBACTAM PHARMACEUTICAL COMPOSITIONS

RELATED APPLICATIONS

This application claims priority to U.S. Provisional Patent Application No. 61/792,092, filed Mar. 15, 2013, and U.S. Provisional Patent Application No. 61/793,007, filed Mar. 15, 2013, both of which are incorporated herein in their entirety.

TECHNICAL FIELD

This disclosure relates to antibacterial compositions comprising ceftolozane and tazobactam.

BACKGROUND

The pharmaceutical antibiotic composition comprising ceftolozane and tazobactam in a 2:1 weight ratio of ceftolozane active to tazobactam acid ("CXA-201") displays potent antibacterial activity, including antibiotic activity against infections caused by many Gram-negative pathogens such as *Pseudomonas aeruginosa* (*P. aeruginosa*), *Escherichia coli* (*E. coli*), *Klebsiella pneumonia* (*K. pneumonia*). In particular, CXA-201 is a pharmaceutical composition being developed for intravenous administration for the treatment of complicated intra-abdominal infections and/or complicated urinary tract infections, and is being evaluated for treatment of pneumonia.

Ceftolozane is a cephalosporin antibacterial agent, also referred to as CXA-101, FR264205, or by chemical names such as (6R,7R)-3-[(5-amino-4-{[(2-aminoethyl)carbamoyl]amino}-1-methyl-1H-pyrazol-2-ium-2-yl)methyl]-7-({(2Z)-2-(5-amino-1,2,4-thiadiazol-3-yl)-2-[(1-carboxy-1-methylethoxy)imino]acetyl}amino)-8-oxo-5-thia-1-azabicyclo[4.2.0]oct-2-ene-2-carboxylate, and 7β-[(Z)-2-(5-amino-1,2,4-thiadiazol-3-yl)-2-(1-carboxy-1-methylethoxyimino)acetamido]-3-{3-amino-4-[3-(2-aminoethyl)ureido]-2-methyl-1-pyrazolio}methyl-3-cephem-4-carboxylate. The antibacterial activity of ceftolozane is believed to result from its interaction with penicillin binding proteins (PBPs) to inhibit the biosynthesis of the bacterial cell wall which acts to stop bacterial replication. Ceftolozane sulfate is a pharmaceutically acceptable ceftolozane salt of formula (I) that can be formulated for intravenous administration or infusion.

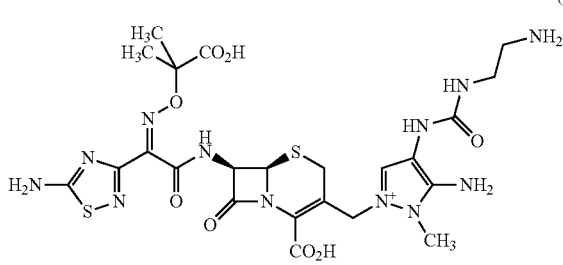

(I)

In CXA-201, ceftolozane is combined with the β-lactamase inhibitor ("BLI") tazobactam. Tazobactam is a BLI against Class A and some Class C β-lactamases, with well-established in vitro and in vivo efficacy in combination with active β-lactam antibiotics. Tazobactam can be combined with ceftolozane as a lyophilized composition obtained by lyophilizing a solution of water, a sodium containing base (e.g., sodium bicarbonate) and the tazobactam acid form of formula (II).

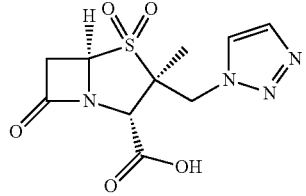

(II)

Pharmaceutical compositions comprising one or more drug substances can be prepared by lyophilization of a solution containing the drug substance(s). Lyophilization is a process of freeze-drying in which water is sublimed from a frozen solution of one or more solutes. Specific methods of lyophilization are described in Remington's Pharmaceutical Sciences, Chapter 84, page 1565, Eighteenth Edition, A. R. Gennaro, (Mack Publishing Co., Easton, Pa., 1990). The formulation of pharmaceutical compositions can be selected to minimize decomposition of the constituent drug substances and to produce a composition that is stable under a variety of storage conditions.

As disclosed herein, compositions formed by lyophilizing ceftolozane and tazobactam demonstrated an increase in total ceftolozane related substance impurities over time of about 31-36% after 3 months at 25 degrees C. (e.g., see data tables in FIGS. 6A and 9A) and about 200-264% after 3 months at 40 degrees C. (e.g., see data tables in FIGS. 6B and 9B). As a result of increasing ceftolozane related substance impurities over time, the amount of ceftolozane in a pharmaceutical composition can decrease prior to placement of a ceftolozane composition within a unit dosage form container. Unit dosage forms that fail to comply with applicable specifications over time, such as the ceftolozane purity or increased amounts of ceftolozane related substances over time, cannot be used to treat patients and must be safely and appropriately discarded. This points to a potential benefit of unit dosage forms of pharmaceutical compositions (e.g., CXA-201 compositions) with reduced levels of ceftolozane related substance impurities for longer periods of time after manufacturing, and methods of manufacturing these unit dosage forms (e.g., to extend the shelf-life of the unit dosage form product).

SUMMARY

Pharmaceutical compositions comprising ceftolozane and tazobactam can be manufactured to reduce the total amount and/or the rate of formation of certain related substances present in the pharmaceutical compositions over time by first combining the ceftolozane and tazobactam within a unit dosage form container (e.g., a vial, bag or other container) in powder form for later reconstitution ("split-fill" presentation), or by providing ceftolozane and tazobactam in separate containers for combination in a fixed dose ratio at a point of patient treatment ("two-container" presentation). In both presentations, the point of first contact of a ceftolozane-containing composition with a tazobactam-containing composition is closer in time to subsequent patient administration than in the products manufactured by processes that combine ceftolozane and tazobactam in a single (e.g., blended) composition prior to filling of the composition(s) into a unit dosage form container. As a result, the time available for formation of ceftolozane related substance impurities within the product is reduced in the products disclosed herein.

The unit dosage form containers can be obtained by a "split-fill" process comprising the steps of: (a) sequential, aseptic filling of the ceftolozane and tazobactam into a unit dosage form container; (b) blanketing the unit dosage form container with an inert gas; and (c) sealing the unit dosage form container.

Alternatively, a product presentation comprising separate unit dosage form containers can be obtained by a "two-container" process comprising the steps of: (a) aseptic filling and sealing of a ceftolozane composition in a first unit dosage form into a first container in the absence of tazobactam; (b) aseptic filling and sealing of a tazobactam composition in a first unit dosage form into a second container in the absence of ceftolozane; and (c) packaging the first container and the second container as a single product for later combination in a fixed dose combination of the ceftolozane composition and the tazobactam composition in a weight ratio of 2:1 between the amount of ceftolozane active and tazobactam free acid. The two-container product presentation can also be obtained by a process comprising the steps of: (a) providing a ceftolozane composition prepared in the absence of tazobactam, (b) providing a tazobactam composition prepared in the absence of ceftolozane, (c) aseptic filling and sealing of the ceftolozane composition in a first unit dosage form into a first container; (d) aseptic filling and sealing of the tazobactam composition in a second unit dosage form into a second container in the absence of ceftolozane; and (e) packaging the first container and the second container as a single product for later combination in a fixed dose combination of the ceftolozane composition and the tazobactam composition in a weight ratio of 2:1 between the amount of ceftolozane active and tazobactam free acid.

Measurements of ceftolozane related substances can be identified as compositions having the retention times for peaks 1-11 in Table 1, as identified by high performance liquid chromatography (HPLC), where HPLC measurements are made using a Develosil column ODS-UG-5; 5 micrometers; 250×4.6 mm, a mobile phase of sodium perchlorate buffer solution (pH 2.5)/$CH_3CN$ 90:10 (v/v) at a 1.0 mL/min flow rate and oven temperature of 45° C. (i.e., as used herein, "related substances").

BRIEF DESCRIPTION OF THE DRAWINGS

FIG. 3 is a table (Table 1) of peaks for the ceftolozane prepared by the lyophilization process in Example 1 obtained by HPLC according to the analytical method of Example 2.

FIG. 4B is a table (Table 2) showing a first composition that can be lyophilized to form a Co-Lyophilized Composition.

FIG. 5 is a table (Table 3) showing a second composition that can be lyophilized to form a Co-Lyophilized Composition.

FIG. 6A is a table (Table 4) showing the amount of various materials identified in Co-Lyophilized Composition of FIG. 5, comprising the related substances at a first temperature (25 degrees C.) as measured by HPLC peak area according to the analytical method of described in Example 2.

FIG. 6B is a table (Table 5) showing the amount of various materials identified in Co-Lyophilized Composition of FIG. 5, at a second temperature (40 degrees C.) as measured by HPLC peak area according to the analytical method of described in Example 2.

FIG. 7 is a table (Table 6) showing in-process testing of blending a composition comprising ceftolozane and tazobactam at three places.

FIG. 8 is a table (Table 7) showing a blended composition comprising ceftolozane and tazobactam.

FIG. 9A is a table (Table 8) showing the amount of various materials identified in a second blended composition of FIG. 7, comprising the Related Substances at a first temperature (25 degrees C.) as measured by HPLC peak area according to the analytical method of described in Example 2.

FIG. 9B is a table (Table 9) showing the amount of various materials identified in a second blended composition of FIG. 8, at a second temperature (40 degrees C.) as measured by HPLC peak area according to the analytical method of described in Example 2.

DETAILED DESCRIPTION

Pharmaceutical compositions comprising ceftolozane (e.g., ceftolozane sulfate) and tazobactam (e.g., tazobactam sodium) can be obtained by processes that reduce the total amount of related substances after the compositions are placed in a unit dosage form container and prior to opening these containers for administration of the product to a patient. The products can be manufactured by methods that avoid contact of ceftolozane and tazobactam prior to placement in a unit dosage form container or prior to formulation of a fixed dose ceftolozane-tazobactam combination product from multiple product containers.

Figure 1A:
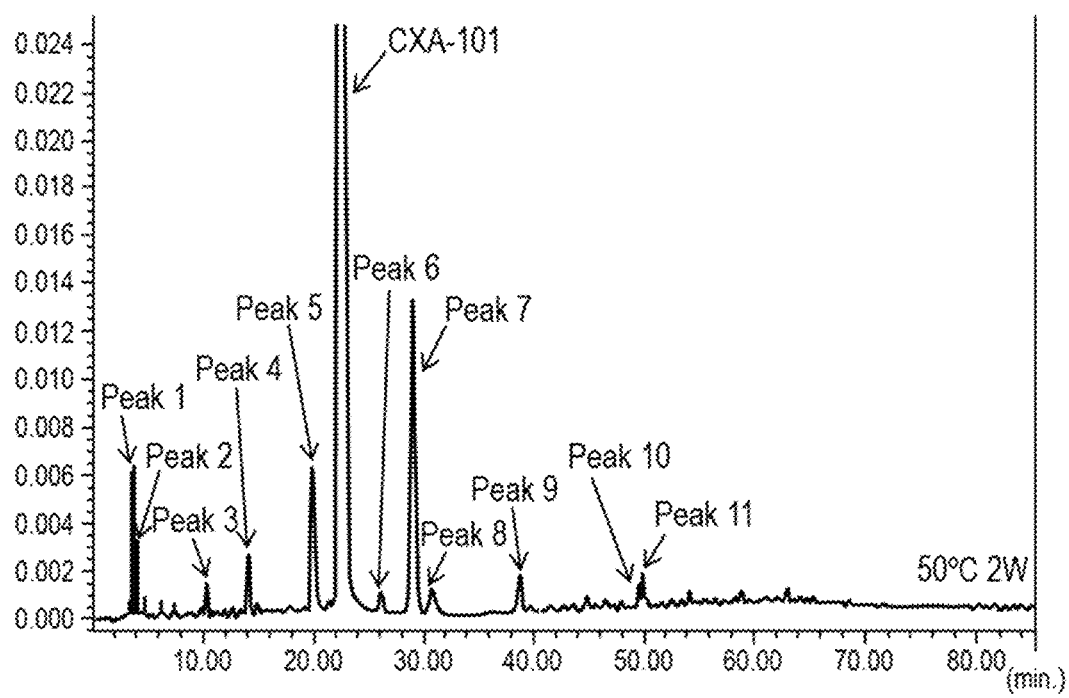
FIGS. 1A and 1B are chromatograms of CXA-101 ceftolozane drug substance obtained from the lyophilization process of Example 1. The chromatograms were obtained according to the analytical method described in Example 2.
Figure 1B:
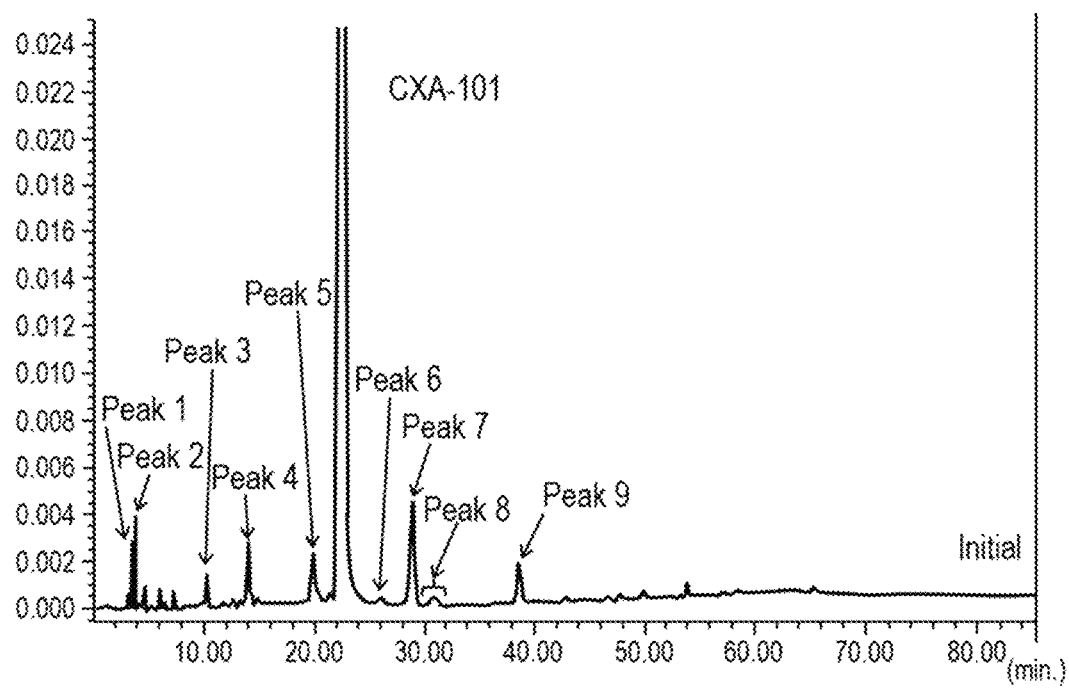

Preferably, products disclosed herein provide less time for formation of ceftolozane Related Substances within the unit dosage form container than alternative product presentations where ceftolozane and tazobactam are brought into contact prior to placement in one or more unit dosage form containers. As used herein, the term "related substances" refers to compositions having the characteristic retention times for peaks 1-11 in Table 1 identified by high performance liquid chromatography (HPLC), where the HPLC measurements are made using a Develosil column ODS-UG-5; 5 micrometers; 250×4.6 mm, a mobile phase of sodium perchlorate buffer solution (pH 2.5)/$CH_3CN$ 90:10 (v/v) at a 1.0 mL/min flow rate and oven temperature of 45° C. Tables 5-6 and 8-9 provide the amounts of Related Substances observed in various samples during certain stability testing. FIGS. 1A and 1B are chromatograms of CXA-101 ceftolozane drug substance obtained from the lyophilization process of Example 1. The chromatograms were obtained according to the analytical method described in Example 2. FIG. 3 is a table of peaks for the ceftolozane prepared by the lyophilization process in Example 1 obtained by HPLC according to the analytical method of Example 2. The unit dosage forms manufactured according to preferred embodiments disclosed herein provide compositions comprising ceftolozane and tazobactam having a total amount of related substances that is less than the drug product specification shown in FIG. 9A under drug product specification (i.e., less than about 7% by HPLC performed by the method of Example 2). More preferably, the total related substances in the unit dosage forms comprising ceftolozane and tazobactam is less than about 2.5% (e.g., about 1.5% or less for t0 measurement in FIG. 6A or about 2% or less for t0 measurements shown in FIG. 9A).

FIG. 8 is a table of an example of a blended composition of ceftolozane and tazobactam that was tested to obtain the data in the tables of FIGS. 9A and 9B. Referring to the data tables in FIGS. 9A and 9B, the amount of related substances in blend compositions were determined by HPLC as described in Example 2, in two different stability tests. The data in the table of FIG. 9A was obtained from a 3 month stability study where the co-lyophilized composition of FIG. 8 was maintained at 25 degrees C. and 60% relative humidity (RH) for 1 and 3 months. The data in the table of FIG. 9B was obtained from a 3 month stability study where the co-lyophilized composition of FIG. 5 was maintained at 40 degrees C. and 60% relative humidity (RH) for 1 and 3 months. The product presentations described herein are based in part on the discovery that compositions prepared by blending separate ceftolozane and tazobactam compositions (e.g., Example 5 and FIGS. 8, 9A and 9B) showed slower rates of formation of the Related Substances than co-lyophilized compositions (e.g., of Example 3 and FIGS. 5, 6A and 6B) during 3 month stability testing, even though the initial amounts of the Related Substances were lower in the co-lyophilized compositions in comparison with those present in the blend compositions.

For example, a composition formed by lyophilizing ceftolozane and tazobactam separately and then blending these components listed in FIG. 8 demonstrated an increase in total ceftolozane related substance impurities (peaks 1-11 measured by HPLC (Example 2) over three months at 25 degrees C. and 60% relative humidity (from T0 to T2 in FIG. 9A) from about 2.0% (i.e., the sum of peaks 1-11 in the t0 column of Table 8, counting "<0.03%" as 0) to about 2.7% (i.e., the sum of peaks 1-11 in the t2 column of Table 8, counting "<0.03%" as 0), corresponding to an increase of about 31% in related substances over three months at 25 degrees C. and 60% relative humidity. A composition formed by lyophilizing ceftolozane and tazobactam separately and then blending these components listed in FIG. 8 demonstrated an increase in total ceftolozane related substance impurities (peaks 1-11 measured by HPLC (Example 2) over three months at 40 degrees C. and 75% relative humidity (from T0 to T2 in FIG. 9B) from about 2% (i.e., the sum of peaks 1-11 in the t0 column of Table 9, counting "<0.03%" as 0) to about 4% (i.e., the sum of peaks 1-11 in the t2 column of Table 9, counting "<0.03%" as 0), corresponding to an increase of about 200% in Related Substances over three months at 40 degrees C. and 75% relative humidity.

A composition formed by co-lyophilizing ceftolozane and tazobactam listed in FIG. 5 demonstrated an increase in total ceftolozane related substance impurities (peaks 1-11) measured by HPLC (Example 2) over three months at 25 degrees C. and 60% relative humidity (from T0 to T2 in FIG. 6A) from about 1.5% (i.e., the sum of peaks 1-11 in the t0 column of Table 4, counting "<0.03%" as 0) to about 2% (i.e., the sum of peaks 1-11 in the t2 column of Table 4, counting "<0.03%" as 0), corresponding to an increase of about 36% in related substances over three months at 25 degrees C. and 60% relative humidity. Similarly, the composition formed by co-lyophilizing ceftolozane and tazobactam as listed in FIG. 5 demonstrated an increase in total ceftolozane related substance impurities over time from about 1.5% related substances at t0 in Table 5 to about 3.9% in Table 5 (corresponding to an increase of 1.5% to 3.9%, or about a 264% increase in related substances over three months at 40 degrees C. and 75% relative humidity).

The rate of increase in related substances for peaks 1-11 was greater in the co-lyophlized ceftolozane-tazobactam sample of Table 3/FIG. 5 than the blended ceftolozane/tazobactam sample of Table 7/FIG. 8 in both 3 month stability tests. The first test was conducted at 25 degrees C. and 60% RH. The blended ceftolozane-tazobactam sample of Table 7/FIG. 8 also showed an increase in related substances of about 31% after 3 months at 40 degrees C., compared to an increase of about 36% for a co-lyophilized composition described in Table 3/FIG. 5 after 3 months at 40 degrees C. under comparable stability testing conditions. The second stability test was performed for 3 months at 40 degrees C. and 75% relative humidity. The blended ceftolozane-tazobactam sample of Table 7/FIG. 8 showed an increase in Related Substances of about 200% after 3 months at 40 degrees C., compared to an increase of about 264% for a co-lyophilized composition described in Table 3/FIG. 5 under comparable stability testing conditions.

Pharmaceutical compositions comprising ceftolozane and tazobactam can be manufactured and formulated to reduce the total amount and/or the rate of formation of certain related substances present in the pharmaceutical compositions over time. In particular, ceftolozane-containing compositions can be manufactured and handled in the absence of contact with tazobactam prior to enclosure within a unit dosage form container, for example by lyophilization of a composition comprising ceftolozane sulfate and a stabilizing agent such as sodium chloride (e.g., 125 mg-500 mg of sodium chloride per 1,000 mg of ceftolozane active equivalent). Tazobactam-containing compositions can be manufactured and handled in the absence of contact with ceftolozane prior to enclosure within a unit dosage form container. Preferably, the compositions are obtained by a process comprising the step of first contacting ceftolozane and tazobactam within a unit dosage form container (e.g., a vial), thereby extending the shelf life of the product in comparison to compositions where tazobactam and ceftolozane are first contacted in a blend outside of the unit dosage form container and subsequently transferred to the unit dosage form container.

Figure 2:
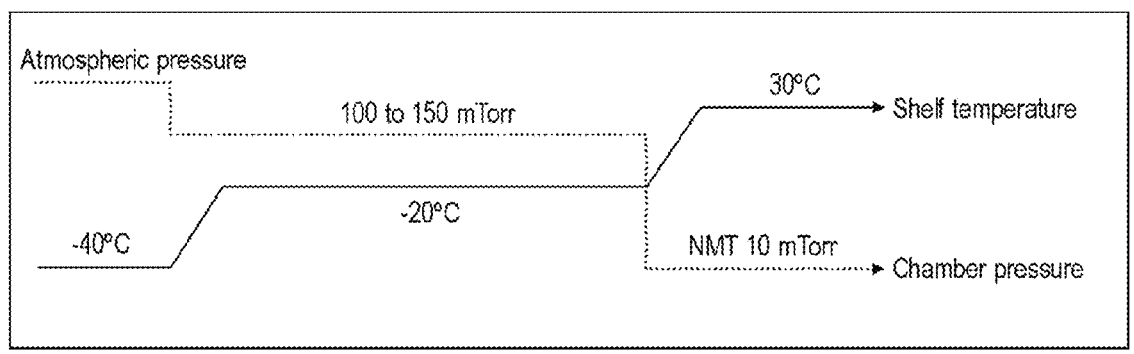
FIG. 2 is a diagram of a lyophilization process for the ceftolozane obtained according to the process described in Example 1.

The pharmaceutical compositions comprising ceftolozane and tazobactam can be prepared by a process wherein the ceftozolane and tazobactam are individually lyophilized in the absence of one another, followed by aseptically combining the individually lyophilized ceftozolane and tazobactam within a unit dosage form container. Alternatively, the pharmaceutical compositions comprising ceftolozane and tazobactam can be prepared by a co-filling process, wherein the ceftozolane and tazobactam are individually lyophilized in the absence of one another, followed by co-filling the individually lyophilized ceftozolane and tazobactam in a vial. In an embodiment of the co-filling method, ceftolozane and tazobactam are sequentially administered into a vial. Specific methods of lyophilization are described in Example 1 and Remington's Pharmaceutical Sciences, Chapter 84, page 1565, Eighteenth Edition, A. R. Gennaro, (Mack Publishing Co., Easton, Pa., 1990). FIG. 2 is a diagram of a lyophilization process for the ceftolozane obtained according to the process described in Example 1.

The products include a ceftolozane composition prepared and handled in the absence of tazobactam by forming a first aqueous solution comprising ceftolozane sulfate and other components including excipients, stabilizers, pH adjusting additives (e.g., buffers) and the like. Non-limiting examples of these additives include sodium chloride, citric acid and L-arginine. For example, the use of sodium chloride results in greater stability; L-arginine is used to adjust pH of the aqueous solution (e.g., to pH 5-7) and to increase the solubility of ceftolozane; and citric acid is used to prevent discoloration of the product, due to its ability to chelate metal ions. Preferably, the first aqueous solution comprises about 125 mg-500 mg sodium chloride per 1,000 mg of ceftolozane active. The ceftolozane can be included as an amount of ceftolozane sulfate of formula (I) containing at least about 1,000 mg ceftolozane active.

The products include a tazobactam composition prepared and handled in the absence of ceftolozane by forming a second solution comprising tazobactam acid. The tazobactam can be included in an amount providing about 500 mg of tazobactam acid per 1,000 mg ceftolozane active (i.e., a 1:2 weight ratio of tazobactam acid to ceftolozane active). Tazobactam is a β-lactamase inhibitor of the structure of formula (II) in its free acid form.

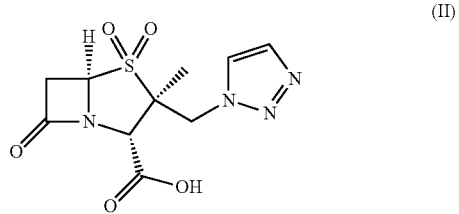 [SMILES: C[C@]1(Cn2ccnn2)[C@H](C(=O)O)N2C(=O)C[C@H]2S1(=O)=O]
(II)

Unless otherwise indicated, tazobactam can be a free acid, a sodium salt, an arginine salt, or a hydrate or solvate thereof.

"Split-Fill" Product Presentation

A first presentation of a ceftolozane-tazobactam antibiotic product is a single unit dosage form container that includes the ceftolozane composition and the tazobactam composition (as described above) first combined (blended) within a unit dosage form container. The single unit dosage form container can be obtained by a "split-fill" process comprising the steps of: (a) sequential, aseptic filling of a ceftolozane composition and a tazobactam composition into a unit dosage form container; (b) blanketing the unit dosage form container with an inert gas; and (c) sealing the unit dosage form container, where the ceftolozane composition is prepared and handled in the absence of tazobactam prior to filling into the unit dosage form container, and the tazobactam composition is prepared and handled in the absence of ceftolozane prior to filling into the unit dosage form container. The unit dosage form container can have any suitable configuration or presentation, including a vial or bag, which is sealed to isolate the product from air outside the container. Preferably, the unit dosage form container includes a means for injecting a liquid (e.g., a self-sealing rubber surface on a cap) into the container, such as saline or water for injection, to reconstitute the product as a solution. The ceftolozane composition is preferably obtained in the absence of tazobactam by a process comprising the step of lyophilizing a solution comprising ceftolozane (e.g., as ceftolozane sulfate) and 125 mg-500 mg sodium chloride per 1,000 mg ceftolozane active. The solution can be an aqueous solution that also includes an alkalizing agent (e.g., L-arginine) and/or a chelating agent (e.g., citric acid). The tazobactam composition is preferably obtained in the absence of ceftolozane by a process comprising the step of lyophilizing a solution comprising tazobactam (e.g., as tazobactam acid) and an alkalizing agent such as sodium bicarbonate or sodium hydroxide. The solution can be an aqueous solution. Alternatively, the tazobactam composition can be a crystalline form of tazobactam such as tazobactam sodium or tazobactam arginine crystal solid forms, not prepared by lyophilization. The ceftolozane composition and the tazobactam composition are first combined within a unit dosage form container, preferably in a weight ratio of 2:1 between the equivalent amounts of ceftolozane active and the amount of tazobactam free acid. Unit dosage forms for the treatment of certain infections (e.g., complicated urinary tract infections and/or complicated intra-abdominal infections) can comprise a total of 1,000 mg of ceftolozane active and a total of 500 mg of tazobactam active. Unit dosage forms for the treatment of other infections (e.g., pneumonia infections) can comprise a total of 2,000 mg of ceftolozane active and a total of 1,000 mg of tazobactam active.

Alternatively, pharmaceutical compositions comprising ceftolozane and tazobactam can be obtained by first combining ceftolozane and tazobactam within a unit dosage form container in a liquid solution, then lyophilizing the solution within the unit dosage form container ("co-lyophilized compositions"). The unit dosage form containers obtained by co-lyophilization within a unit dosage form container can include (e.g., up to about 1%) an additional substance having an HPLC retention time of about 1.22 relative to that of ceftolozane (see, e.g., FIG. 6A data showing the presence RRT 1.22 compound at 25 degrees C.). Pharmaceutical compositions comprising ceftolozane and tazobactam prepared by either blending or co-filling processes (e.g., as described in Example 5) have a different composition compared to compositions prepared by co-lyophilization (e.g., as described in Example 3). In contrast, ceftolozane and tazobactam individually lyophilized prior to blending, led to a pharmaceutical composition comprising a much lower amount of the compound of formula (III):

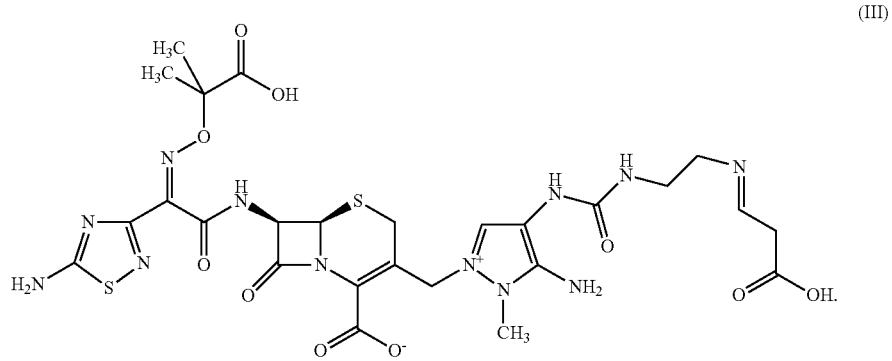 [SMILES: Cn1c(N)c(NC(=O)NCC/N=C/CC(=O)O)c[n+]1CC1=C(C(=O)[O-])N2C(=O)[C@@H](NC(=O)/C(=N\OC(C)(C)C(=O)O)c3nsc(N)n3)[C@H]2SC1]
(III)

The compound of formula (III) has a relative retention time (RRT) of 1.22 (relative to ceftolozane using the HPLC analysis). This compound is also referred to herein as "the compound RRT 1.22." Without being bound by theory, the compound RRT 1.22 can be formed by a reaction between ceftolozane and formylacetic acid, a by-product of tazobactam as illustrated in Marunaka et al. (Chem. Pharm. Bull. 1988, Vol. 36 (11), pp. 4478-4487.

Figure 4A:
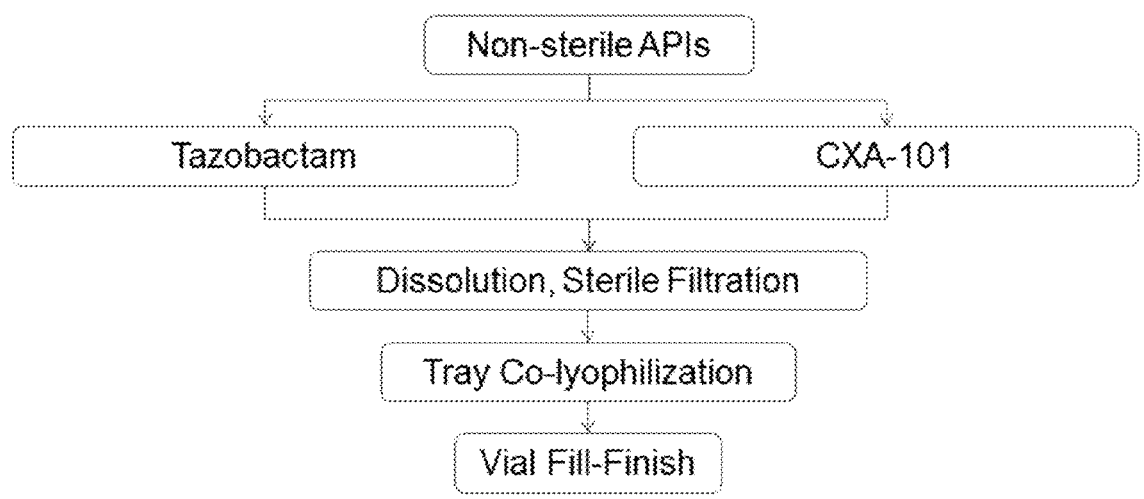
FIG. 4A is a schematic showing a process for making a Co-Lyophilized Composition with ceftolozane and tazobactam.

The lyophilization of a composition within the unit dosage form container is based in part on the discovery that compositions having lower initial amounts of total Related Substances were obtained by lyophilizing a solution comprising ceftolozane and tazobactam. FIG. 4A is a schematic showing a process for making the compound of formula (III) with ceftolozane and tazobactam. The co-lyophilized compositions can be obtained by a process comprising the steps of: (a) forming a solution (e.g., and aqueous solution) comprising ceftolozane (e.g., ceftolzoane sulfate), and tazobactam (e.g., tazobactam acid), and (b) lyophilizing the solution to obtain the Co-Lyophilized Compositions. Preferably, the solution prior to lyophilization comprises ceftolozane, tazobactam, and about 125-500 mg of sodium chloride per 1,000 mg of ceftolozane active. More preferably, the solution further comprises L-arginine and/or citric acid. Most preferably, the solution comprises ceftolozane and tazobactam in a weight ratio of about 2:1 between the amount of ceftolozane active and the amount of tazobactam acid in the solution prior to lyophilization. The solution can have a pH of about 5-7 (e.g., by including an amount of L-arginine to provide the pH of 5-7, e.g., 6-7). The solution can further comprise sodium bicarbonate and/or other excipients. Examples of aqueous solutions suitable for lyophilization to obtain Co-Lyophilized compositions are provided in the tables in FIG. 4B and FIG. 5. The lyophilization cycle can be performed by any suitable method effective to remove the water or other solvent in the solution. For example, the lyophilization can be performed according to the program in FIG. 2.

Referring to the data tables in FIGS. 6A and 6B, the amount of related substances in co-lyophilized compositions were determined by HPLC as described in Example 2, in two different stability tests. The data in the table of FIG. 6A was obtained from a 3 month stability study where the co-lyophilized composition of FIG. 5 was maintained at 25 degrees C. and 60% relative humidity (RH) for 1 and 3 months. The total amount of related substances in the sample rose from an initial amount of about 1.46% to about 1.98% after 3 months (i.e., about a 36% increase). The data in the table of FIG. 6B was obtained from a 3 month stability study where the co-lyophilized composition of FIG. 5 was maintained at 40 degrees C. and 60% relative humidity (RH) for 1 and 3 months. The total amount of Related Substances in the sample rose from an initial amount of about 1.46% to about 3.85% after 3 months (i.e., about a 264% increase).

Two-Container Product Presentation

A two-container product presentation can be obtained by separately packaging ceftolozane in the absence of tazobactam, and tazobactam in the absence of ceftolozane. The second product presentation comprises separate unit dosage form containers obtained by a "two-container" process comprising the steps of: (a) aseptic filling and sealing of a ceftolozane composition in a first unit dosage form into a first container in the absence of tazobactam; (b) aseptic filling and sealing of a tazobactam composition in a first unit dosage form into a second container in the absence of ceftolozane; and (c) packaging the first container and the second container as a single product for later combination in a fixed dose combination of the ceftolozane composition and the tazobactam composition in a weight ratio of 2:1 between the amount of ceftolozane active and tazobactam free acid. These steps can be performed in any order. The two-container product presentation can also be obtained by a process comprising the steps (performed in any order) including: (a) providing a ceftolozane composition prepared in the absence of tazobactam, (b) providing a tazobactam composition prepared in the absence of ceftolozane, (c) aseptic filling and sealing of the ceftolozane composition in a first unit dosage form into a first container; (d) aseptic filling and sealing of the tazobactam composition in a second unit dosage form into a second container in the absence of ceftolozane; and (e) packaging the first container and the second container as a single product for later combination in a fixed dose combination of the ceftolozane composition and the tazobactam composition in a weight ratio of 2:1 between the amount of ceftolozane active and tazobactam free acid.

In the two-container product presentation, the blended composition is formed by first contacting ceftolozane and tazobactam after opening the containers (e.g., at a location for treating a patient, such as a hospital pharmacy). The two-container product presentation includes a first sealed container comprising ceftolozane obtained and provided in the absence of tazobactam and a second sealed container comprising tazobactam comprising tazobactam obtained and provided in the absence of ceftolozane. The first container and the second container can be opened and the ceftolozane and tazobactam compositions can be combined in a fixed weight ratio corresponding to a 2:1 weight ratio between the amount of ceftolozane active and the amount of tazobactam free acid in the first and second compositions, respectively. The resulting blended composition comprising ceftolozane and tazobactam can be reconstituted in a pharmaceutically acceptable liquid (e.g., physiological saline, or water for injection) for intravenous administration to a patient in need thereof.

The two-container unit dosage form can be obtained by a process comprising the steps of: (a) aseptic filling of a ceftolozane composition into a first container; (b) blanketing the first container with an inert gas; (c) sealing the first container, where the ceftolozane composition is prepared and handled in the absence of tazobactam prior to filling into the first container; (d) aseptic filling of a tazobactam composition into a second container; (e) blanketing the second container with an inert gas; (f) sealing the second container, where the tazobactam composition is prepared and handled in the absence of ceftolozane prior to filling into the unit dosage form container; and (g) packaging the first container and the second container together in a unit dosage form package with instructions for combining the ceftolozane composition and the tazobactam composition in a fixed dose combination prior to administration to a patient.

The containers and packages can have any suitable configuration or presentation, including a vial or bag, which is sealed to isolate the ceftolozane composition and the tazobactam composition both from each other and from air outside the containers. The ceftolozane composition and the tazobactam composition can be combined after opening each respective container either in powder or liquid form in a fixed dose ratio. Preferably, each container includes a means for injecting a liquid (e.g., a self-sealing rubber surface on a cap) into the container, such as saline or water for injection, to reconstitute the product as a solution. The ceftolozane composition in a first container is preferably obtained in the absence of tazobactam by a process comprising the step of lyophilizing a solution comprising ceftolozane (e.g., as ceftolozane sulfate) and 125 mg-500 mg sodium chloride per 1,000 mg ceftolozane active. The solution can be an aqueous solution that also includes an alkalizing agent (e.g., L-arginine) and/or a chelating agent (e.g., citric acid). The tazobactam composition in the second container is preferably obtained in the absence of ceftolozane by a process comprising the step of lyophilizing a solution comprising tazobactam (e.g., as tazobactam acid) and an alkalizing agent such as sodium bicarbonate or sodium hydroxide. The solution can be an aqueous solution. Alternatively, the tazobactam composition in the second container can be a crystalline form of tazobactam such as tazobactam sodium or tazobactam arginine crystal solid forms, not prepared by lyophilization.

The ceftolozane composition and the tazobactam composition are first combined after packaging of the two-container unit dosage form, preferably in a weight ratio of 2:1 between the equivalent amounts of ceftolozane active and the amount of tazobactam free acid. Unit dosage forms for the treatment of certain infections (e.g., complicated urinary tract infections and/or complicated intra-abdominal infections) can comprise a total of 1,000 mg of ceftolozane active and a total of 500 mg of tazobactam active (obtained from at least two containers). Unit dosage forms for the treatment of other infections (e.g., pneumonia infections) can comprise a total of 2,000 mg of ceftolozane active and a total of 1,00 mg of tazobactam active (obtained from at least two containers).

Additional Pharmaceutical Compositions and Methods of Treatment

Pharmaceutical compositions in one or more unit dosage forms can be co-lyophilized compositions and/or blended compositions comprising ceftolozane and tazobactam and can be formulated to treat infections by parenteral administration (including subcutaneous, intramuscular, and intravenous) administration.

Pharmaceutical compositions may additionally comprise excipients, stabilizers, pH adjusting additives (e.g., buffers) and the like. Non-limiting examples of these additives include sodium chloride, citric acid and L-arginine. For example, the use of sodium chloride results in greater stability; L-arginine is used to adjust pH and to increase the solubility of ceftolozane; and citric acid is used to prevent discoloration of the product, due to its ability to chelate metal ions. In one particular embodiment, the pharmaceutical compositions described herein are formulated for administration by intravenous injection or infusion.

The amount of the compound of formula (III) can be increased in the composition as disclosed herein (e.g., by heating a sample produced by co-lyophlization of tazobactam and ceftolozane in an aqueous solution, followed by heating of the lyophilized product to increase the amount of the compound of formula (III)). The compound of formula (III) can also be isolated from compositions comprising ceftolozane and tazobactam and then re-combined with ceftolozane and/or tazobactam to form compositions with desired concentrations of the compound of formula (III). Pharmaceutical compositions can include less than 0.03%, 0.05%, 0.13%, 0.15%, 0.30%, 0.38%, 0.74% or 0.97% of the compound of formula (III), as measured by HPLC. Other pharmaceutical compositions can include a range from less than about 0.03% (e.g., see minimum detected amounts in Tables 4-5) to about 1.0% (e.g., maximum detected amount of RRT 1.22 in Tables 4-5) or more of the compound of formula (III) including compositions comprising 0.03%-0.05%, 0.05%, 0.05%-0.13%, 0.05%-0.15%, 0.03%-0.13%, 0.05%- of the compound of formula (III), where the % of the compound of formula (III) as measured by HPLC using a Develosil column ODS-UG-5; 5 micrometers; 250×4.6 mm, a mobile phase of sodium perchlorate buffer solution (pH 2.5)/$CH_3CN$ 90:10 (v/v) at a 1.0 mL/min flow rate and oven temperature of 45° C. The pharmaceutical antibiotic compositions can include ceftolozane or a pharmaceutically acceptable salt thereof and an amount of the compound of formula (III). Compositions can also be made comprising the compound of formula (III) in the absence of tazobactam and/or in the absence of ceftolozane.

In one example, a pharmaceutical composition in a unit dosage form container comprises ceftolozane sulfate and tazobactam in a ratio of 1,000 mg ceftolozane active per 500 mg of tazobactam active and up to about 1%, more preferably up to about 0.03%-0.05%, of a compound of formula (III) as measured by HPLC using a Develosil column ODS-UG-5; 5 micrometers; 250×4.6 mm, a mobile phase of sodium perchlorate buffer solution (pH 2.5)/$CH_3CN$ 90:10 (v/v) at a 1.0 mL/min flow rate and oven temperature of 45° C. The pharmaceutical composition obtained by a process comprising the steps of lyophilizing an aqueous solution comprising ceftolozane sulfate, tazobactam (e.g., tazobactam free acid and/or tazobactam sodium), 125 mg to 500 mg of sodium chloride per 1,000 mg of ceftolozane active, L-arginine and/or citric acid in an amount effective to adjust the pH of the first aqueous solution to 5-7 (e.g., 6-7) prior to lyophilization to obtain a first lyophilized ceftolozane composition.

Alternatively, the pharmaceutical composition comprising up to about 1% of a compound of formula (III) as measured by HPLC (e.g., with HPLC using a Develosil column ODS-UG-5; 5 micrometers; 250×4.6 mm, a mobile phase of sodium perchlorate buffer solution (pH 2.5)/$CH_3CN$ 90:10 (v/v) at a 1.0 mL/min flow rate and oven temperature of 45° C.) can be obtained by a process comprising the steps of: (a) lyophilizing a first aqueous solution in the absence of tazobactam, the first aqueous solution comprising ceftolozane sulfate, 125 mg to 500 mg of sodium chloride per 1,000 mg of ceftolozane active, L-arginine and/or citric acid in an amount effective to adjust the pH of the first aqueous solution to 5-7 (e.g, 6-7) prior to lyophilization to obtain a first lyophilized ceftolozane composition; (b) lyophilizing a second solution in the absence of ceftolozane, the second solution comprising tazobactam being lyophilized to form a second lyophilized tazobactam composition; and (c) blending within a unit dosage form container the first lyophilized ceftolozane composition, the second lyophilized tazobactam composition and a composition comprising the compound of formula (III).

The pharmaceutical antibiotic compositions can be provided in a unit dosage form container (e.g., in a vial or bag). The unit dosage form can be dissolved with a pharmaceutically acceptable carrier, and then intravenously administered. A unit dosage form of a pharmaceutical composition can be formulated for parenteral administration for the treatment of complicated intra-abdominal infections or complicated urinary tract infections can enclose a pharmaceutical composition comprising the compound of formula (III). Compositions can be produced by co-lyophilization or blending in a vial (e.g., Example 1). For example, an aqueous solution comprising ceftolozane and tazobactam in a vial can be lyophilized to obtain a unit dosage form.

In one aspect, provided herein is a method for the treatment of bacterial infections in a mammal, comprising administering to said mammal a therapeutically effective amount of a pharmaceutical composition prepared according to the methods described herein. A method for the treatment of bacterial infections in a mammal can comprise administering to said mammal a therapeutically effective amount of a pharmaceutical composition comprising ceftolozane sulfate and sodium chloride. Non-limiting examples of bacterial infections that can be treated by the methods of the invention include infections caused by: aerobic and facultative gram-positive microorganisms (e.g., *Staphylococcus aureus, Enterococcus faecalis, Staphylococcus epidermidis, Streptococcus agalactiae, Streptococcus pneumonia, Streptococcus pyogenes*, Viridans group streptococci), aerobic and facultative gram-negative microorganisms (e.g., *Acinetobacter baumanii, Escherichia coli, Haemophilus influenza, Klebsiella pneumonia, Pseudomonas aeruginosa, Citrobacter koseri, Moraxella catarrhalis, Morganella morganii, Neisseria gonorrhoeae, Proteus mirabilis, Proteus vulgaris, Serratia marcescens, Providencia stuartii, Providencia rettgeri, Salmonella enterica*), gram-positive anaerobes (*Clostridium perfringens*), and gram-negative anaerobes (e.g., *Bacteroides fragilis* group (e.g., *B. fragilis, B. ovatus, B. thetaiotaomicron*, and *B. vulgates*), *Bacteroides distasonis, Prevotella melaninogenica*). In certain embodiments of the methods described herein, bacterial infection is associated with one or more of the following conditions: complicated intra-abdominal infections, complicated urinary tract infections (cUTIs) and pneumonia (e.g., community-acquired, or nosocomial pneumonia). Community-acquired pneumonia (moderate severity only) can include infections caused by piperacillin-resistant, beta-lactamase producing strains of *Haemophilus influenza*. Nosocomial pneumonia (moderate to severe) caused by piperacillin-resistant, beta-lactamase producing strains of *Staphylococcus aureus* and by *Acinetobacter baumanii, Haemophilus influenzae, Klebsiella pneumoniae*, and *Pseudomonas aeruginosa*.

As used herein, "treating," "treat," or "treatment" describes the management and care of a patient for the purpose of combating a disease, condition, or disorder and includes the administration of a pharmaceutical composition of the present invention to alleviate the symptoms or complications of a disease, condition or disorder, or to reduce the extent of the disease, condition or disorder. The term "treat" can also include treatment of a cell in vitro or an animal model.

By a "therapeutically effective amount" of a compound of the invention is meant a sufficient amount of the compound to treat the disorder (e.g., bacterial infection). The specific therapeutically effective amount that is required for the treatment of any particular patient or organism (e.g., a mammal) will depend upon a variety of factors including the disorder being treated and the severity of the disorder; the activity of the specific compound or composition employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts (see, for example, Goodman and Gilman's, "The Pharmacological Basis of Therapeutics", Tenth Edition, A. Gilman, J. Hardman and L. Limbird, eds., McGraw-Hill Press, 155-173, 2001, which is incorporated herein by reference in its entirety). The therapeutically effective amount for a given situation can be readily determined by routine experimentation and is within the skill and judgment of the ordinary clinician.

As used herein, "1000 mg ceftolozane" refers to an amount of ceftolozane that is considered a bioequivalent by the United States Food and Drug Administration (FDA), i.e. for which 90% CI of the relative mean Cmax, AUC(0-t) and AUC(0-∞) is within 80.00% to 125.00% of the reference formulation in the fasting state (see: "Guidance for Industry: Bioavailability and Bioequivalence Studies for Orally Administered Drug Products—General Considerations". Center for Drug Evaluation and Research, United States Food and Drug Administration, 2003).

As used herein, the term "ceftolozane active" refers to active portion of a salt form of ceftolozane, the free base form of ceftolozane.

As used herein, the term "tazobactam active" refers to the active portion of a salt form of tazobactam, tazobactam free acid form.

As used herein, "1,000 mg of ceftolozane as ceftolozane active" refers to an amount of ceftolozane sulfate effective to provide 1,000 mg of ceftolozane. The amount of sodium per gram of ceftolozane activity in a pharmaceutical composition containing ceftolozane sulfate and sodium chloride can be calculated using the relevant molecular weights of ceftolozane, ceftolozane sulfate, sodium chloride and sodium.

ILLUSTRATIVE EXAMPLES OF SELECTED EMBODIMENTS OF THE INVENTION

Example 1

Manufacturing Procedure of Bulk (Tray) Lyophilized Ceftolozane

There are four main steps in the manufacture of CXA-101 bulk drug product: dissolution, sterile filtration, bulk lyophilization, and packaging into Sterbags®. These four main steps are composed of a total of 20 minor steps. The CXA-101 bulk drug product manufacturing process is presented below.

I. Dissolution
  1. The prescribed amount of water for injection ("WFI") is charged into the dissolution reactor.
  2. A prescribed amount of citric acid is added.
  3. The solution is cooled at 5° C. to 10° C.
  4. A prescribed amount of CXA-101 drug substance is added to the solution.
  5. A prescribed amount of L-arginine is slowly added to the solution.
  6. A check for complete dissolution is performed. Solution pH is verified to be in the target range of 6.5 to 7.0.
  7. A prescribed amount of sodium chloride is added to the solution.
  8. A check for complete dissolution is performed. Solution pH is verified to be in the target range of 6.0 to 7.0. If the pH is out of this range adjust with either L-Arginine or citric acid.
  9. WFI is added to bring the net weight to 124.4 kg and the solution is mixed well.
  10. Samples are withdrawn for testing of final pH.

II. Sterile Filtration
  11. The solution is passed through the filter (pore size 0.45 µm) followed by double filters (pore size 0.22 µm) onto a shelf on the Criofarma lyophilizer.
  12. The line is washed with WFI.
  13. The washing solution is passed from Step 12 through sterile filtration.

III. Bulk Lyophilization
  14. The washing solution is loaded onto a separate shelf in the lyophilizer (and later discarded).
  15. The solution is lyophilized until dry.
  16. The product shelf is cooled to 20° C.±5° C.

IV. Packaging into Sterbags®
  17. The lyophilized bulk drug product powder is milled.
  18. The milled powder is sieved.
  19. The sieved powder is blended for 30 minutes.
  20. The powder is then discharged into Sterbags®

Prefiltration and Sterile-Filtration

Filtrate the compounded solution with a sterile filter-set which consists of a 0.2 um polyvinylidene fluoride membrane filter (Durapore®, Millipore) and a 0.1 urn polyvinylidene fluoride membrane filter (Durapore®, Millipore) connected in tandem. Confirm the integrity of each filter before and after the filtration. Take approximately 100 mL of the filtrate in order to check bioburden.

Filter the prefiltered compounded solution through a sterile filter-set which consists of a 0.2 um polyvinylidene fluoride membrane filter and a 0.1 urn polyvinylidene fluoride membrane filter connected in tandem, and introduce the final filtrate into an aseptic room. Confirm the integrity of each filter before and after the filtration.

Processing of Vial, Stopper and Flip-Off Cap

Wash a sufficient quantity of 28 mL vials with water for injection and sterilize the washed vials by a dry-heat sterilizer. Then transfer the sterilized vials into a Grade A area located in an aseptic room.

Wash a sufficient quantity of stoppers with, water for injection. Sterilize and dry the washed stoppers by steam sterilizer. Then transfer the sterilized stoppers into a Grade A area located in an aseptic room.

Sterilize a sufficient quantity of flip-off caps by steam sterilizer. Then transfer the sterilized flip-off caps into a Grade A or B area located in an aseptic room.

Filling and Partially Stoppering

Adjust the fill weight of the filtered compounded solution to 11.37 g (corresponds to 10 mL of the compounded solution), then start filling operation. Check the filled weight in sufficient frequency and confirm it is in target range (11.37 g±1%, 11.26 to 11.43 g). When deviation from the control range (11.37 g±2%, 11.14 to 11.59 g) is occurred, re-adjust the filling weight.

Immediately after a vial is filled, partially stopper the vial with a sterilized stopper. Load the filled and partially stoppered vials onto the shelves of a lyophilizer aseptically.

Lyophilization to Crimping, Visual Inspection, Labeling and Packaging

After all filled and partially stoppered vials are loaded into a lyophilizer, start the lyophilization program shown in FIG. 2. Freeze the loaded vials at −40° C. and keep until all vials freeze. Forward the program to primary drying step (shelf temperature; −20° C., chamber pressure; 100 to 150 mTorr). Primary drying time should be determined by monitoring the product temperature. Forward the program to secondary drying step (shelf temperature; 30° C., chamber pressure; not more than 10 mTorr) after completion of the primary drying step. After all vials are dried completely, return the chamber pressure to atmospheric pressure with sterilized nitrogen. Then stopper vials completely.

Unload the lyophilized vials from the chamber and crimp with sterilized flip-off caps.

Subject all crimped vials to visual inspection and label and package all passed vials.

Example 2

Analytical HPLC Method

A. Operative Conditions

| Column | Develosil ODS-UG-5; 5 μm, 250 × 4.6 mm (Nomura Chemical, Japan) |
|---|---|
| Mobile phase | Sodium Perchlorate Buffer Solution (PH 2.5)/CH$_3$CN 90:10 (v/v) |
| Flow rate | 1.0 mL/min |
| Wavelength | 254 nm |
| Injection volume | 10 μL |
| Oven Temperature | 45° C. |
| Run Time | 85 minutes |

| Gradient Profile: | Time (min) | A % | B % |
|---|---|---|---|
| | 0 | 75 | 25 |
| | 30 | 70 | 30 |
| | 60 | 0 | 100 |
| | 85 | 0 | 100 |
| | 85.1 | 75 | 25 |
| | 110 | 75 | 25 |

B. Mobile Phase Preparation.

Sodium Perchlorate Buffer Solution was made by dissolving 14.05 g of sodium perchlorate Monohydrate in 1000.0 mL of water followed by adjusting pH to 2.5 with diluted perchloric acid (1 in 20).

Mobile Phase was then made by mixing Sodium Perchlorate Buffer Solution (pH 2.5) and acetonitrile in the ratio 90:10 (v/v).

Sodium Acetate Buffer Solution pH 5.5 (Diluent) was made by dissolving 1.36 g of sodium acetate trihydrate in 1000.0 mL of water followed by adjusting to pH 5.5 with diluted acetic acid (1 in 10).

C. Sample Preparation.

Sample solution: dissolve 20.0 mg, exactly weighed, of Sample, in 20.0 mL of water (Prepare just before injection into HPLC system).

System Suitability Solution (1%): take 1.0 mL of the Sample Solution (use first sample if more are present) and transfer into a 100.0 mL volumetric flask, dilute with water to volume and mix.

D. HPLC Analysis Procedure

1. Inject Blank (water)
2. Inject System Suitability Solution and check for tailing factor and theoretical plate number for CXA-101 peak:

The tailing factor must not be greater than 1.5

Theoretical plates number must not be less than 10000
3. Inject Sample Solution
4. Inject System Suitability Solution and check for tailing factor and theoretical plate number for CXA-101 peak.

The tailing factor must not be greater than 1.5

Theoretical plates number must not be less than 10000
5. Identify the peaks of related substances in the sample chromatogram based on the reference chromatogram reported in FIGS. 1A and 1B or, alternatively, on the basis of the RRT values reported in Table 1 (FIG. 3). The material for "Peak 1" in the Table 1 of FIG. 3, with a retention time of about 0.14 relative to ceftolozane is believed to have the chemical structure of formula (II):

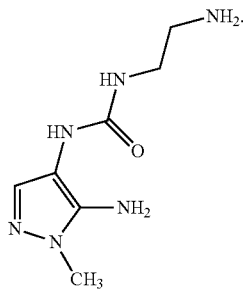

E. Calculations
I. Report for each related substance is amount as expressed by area percent.

$$C_i = \frac{A_i \times 100}{A_t + \Sigma A_i}$$

wherein:
$C_i$=Amount of related substance i in the Sample, area %
$A_i$=Peak area of related substance i in the Sample chromatogram
$A_t$=Area of CXA-101 peak in the Sample chromatogram
$A_t+\Sigma A_i$=Total peaks area in the Sample chromatogram
Consider as any Unspecified Impurity, each peak in the chromatogram except CXA-101, peaks from 1 to 11 and every peak present in the blank chromatogram and report the largest.
II. Report the total impurities content as expressed by the following formula:

$$C_T = \frac{A_i \times 100}{A_t + \Sigma A_i}$$

wherein:
$C_T$=total impurities content in the Sample, area %
$A_t$=area of CXA-101 peak in the sample chromatogram
$\Sigma A_i$=total peak areas of impurities in the sample chromatogram Example 3

Manufacturing Combination Product (Tazobactam and Ceftolozane) by Co-Lyophilization Compositions comprising the compound of formula (III) were prepared by the process shown in FIG. 4A by (a) forming an aqueous solution comprising the components in Table 3 (FIG. 5), and (b) lyophilizing the aqueous solution. Sodium content was approximately 78 mg/g of tazobactam in drug product after lyophilization. Water was removed during the lyophilization process and is controlled at no more than 4% by weight.

Example 4

Assessment of Blend Combination Drug Product

A. Preparation of Blend Combination Drug Product
The blend drug product was prepared, as described above in Example 3, on lab scale by use of a small blender. The composition of the blend drug product is shown in Table 3, FIG. 5. The CXA-101 was obtained by lyophilization of ceftolozane sulfate in the absence of tazobactam, and the tazobactam sodium material was obtained by lyophilization of tazobactam prior to blending of the ceftolozane and tazobactam components.
B. Stability Test
The sample prepared herein (Example 4A) was put into a stability study. Tables 4 (FIG. 6A) and 5 (FIG. 6B) are representative examples that summarize the results at 25° C./RH=60% and 40° C./RH=75% after one month (T1) and three months (T2). Samples were analyzed using a HPLC method as described in Example 1.
C. Conclusion
The data at both 25° C. and at 40° C. have shown that the blending process inhibits formation of amounts of the impurity RRT=1.22 to below the detection limit of the HPLC method of Example 2.

Example 5

Manufacturing of Combination Product (Tazobactam and CXA-101) by Blending Sterile Dry Blending of Bulk Lyophilized Ceftolozane and Bulk Lyophilized Tazobactam The CXA-101 produced by Example 1 is blended with lyophilized tazobactam. A low energy drum blender that agitates the material by tumbling and also moving the bed up and down is used. For CXA-101/tazobactam for injection, the blender was charged with 23.4 kg of CXA-101 bulk product, and 5.4 kg of tazobactam bulk product. Both the CXA-101 and tazobactam were individually lyophilized beforehand. The material was blended for 180 minutes. In-process tests of content assay for both CXA-101 and tazobactam were performed to assess the homogeneity using the samples of blend materials taken from three places. The RSD for each of CXA-101 and tazobactam content assay was no greater than 2% and the RSD for the ratio of CXA-101/tazobactam was no greater than 2.2%. (See Table 6 in FIG. 7).
The blended powder is then discharged into Sterbags®.

Example 6

Co-Lyophilization of Ceftolozane and Tazobactam Produces the Compound of Formula (III) (RRT 1.22)

The co-lyophilized combo drug product was prepared as described above in Example 3. The formulation composition of the co-lyophilized combo drug product is shown in FIG. 8 (Table 7). This sample was maintained at 25° C./RH=60% and 40° C./RH=75% after one month (T1) and three months (T2). Samples were analyzed using a HPLC method as described in Example 2. The data for analysis of the samples by HPLC is shown in the tables in FIG. 9A (Table 4: Stability data of Co-Lyo Combo Drug Product at 25° C.) and FIG. 9B (Table 5: Stability data Co-Lyo Combo Drug Product at 40° C.). The presence of the compound of Formula (III) was identified has having a retention time of about 1.22 as measured by HPLC (see Example 2). RRT=1.22 was observed in co-lyophilized drug product. The compound of formula (III) is believed to be formed by a reaction between ceftolozane and formylacetic acid, which was a degradation product of tazobactam. The amount of the compound of formula (III) in a composition comprising ceftolozane and tazobactam can be increased over time at 25° C. and at 40° C.

A new impurity having RRT=1.22 was observed in co-lyophilized drug product. The impurity was identified as a degradation product of formula (III) which was formed by a reaction between ceftolozane and formylacetic acid, which was a degradation product of tazobactam. The stability data at 25° C. and at 40° C. have shown that the impurity increases over time.

Example 7

Assessment of Blend Combination Drug Product

A. Preparation of Blend Combination Drug Product

The blend drug product was prepared, as described above in Example 5, on lab scale by use of a small blender. The composition of the blend drug product is shown in Table 7. The CXA-101 was obtained by lyophilization of ceftolozane sulfate in the absence of tazobactam, and the tazobactam sodium material was obtained by lyophilization of tazobactam prior to blending of the ceftolozane and tazobactam components.

B. StabilityTest

The sample prepared herein (Example 7A) was put into stability study. The following Tables 8 and 9 (FIGS. 9A and 9B) are representative examples that summarize the results at 25° C./RH=60% and 40° C./RH=75% after one month (T1) and three months (T2). Samples were analyzed using a HPLC method as described in Example 2.

C. Conclusion

The data at both 25° C. and at 40° C. have shown that the blending process completely inhibits formation of the impurity RRT=1.22.

Example 8

Screening of Stabilizing Agents

A stability study of Combo Drug Product for Injection bulk drug product was carried out at long term storage conditions (e.g., 25° C./60% RH), in accordance with ICH guidelines. This formal stability study examined the effect of temperature and humidity on CXA-101/tazobactam for Injection bulk drug product stability when stored in the container closure configuration of Sterbag®.

A stability study of Combo Drug Product for Injection finished drug product was carried out at long term storage conditions (e.g., 25° C., 60% RH), and an accelerated stability condition (e.g., 40° C./75% RH), in accordance with ICH guidelines. This formal stability study examined the effect of temperature and humidity on CXA-101/tazobactam product stability in the container closure configuration of the finish product vial.

Example 9

Preferred Pharmaceutical Composition Comprising Ceftolozane and Tazobactam

Pharmaceutical compositions comprising ceftolozane and tazobactam with less than 0.15% (measured by HPLC according to Example 2) of the compound of formula (III) can be obtained as described herein.

TABLE 10

Excipients Used in Ceftolozane Composition

| Component | Function | Amount, mg/Vial | Concentration in Infusion Solution, % | Rationale for Inclusion | Inactive Ingredients Database (IID) Range |
| --- | --- | --- | --- | --- | --- |
| Citric acid | Chelating agent | 21 | 0.02 | Used to prevent discoloration and degradation | 0.0025 to 50% |
| Sodium Chloride | Stabilizing agent | 487 | 0.49 | Used as a stabilizing agent for ceftolozane sulfate | 0.187 to 45% |
| L-arginine | Alkalizing agent | 600[i] Q.S. for pH adjustment | 0.60 | Used to adjust ceftolozane solution pH | 0.29 to 88% |

[i]L-arginine is added as needed to achieve pH 6.5 ± 0.5; 600 mg per vial is considered a representative total amount.

TABLE 11

Unit Compositions of Ceftolozane/Tazobactam for Injection, 1000 mg/500 mg

| Component | | Function | Nominal Composition mg per Vial |
| --- | --- | --- | --- |
| Ceftolozane composition[1] | Ceftolozane Sulfate | Active | 1147 |
| | Citric Acid, Anhydrous | Chelating Agent | 21 |
| | Sodium Chloride | Stabilizing Agent | 487 |
| | L-Arginine | Alkalizing Agent | 600[2] Q.S. for pH adjustment |
| Tazobactam Sodium[3] | | Active | 537 |
| Nitrogen | | Processing Aid[ii] | Q.S. |
| Total Weight | | | 2792 |

[1]Actual amount of ceftolozane will vary based on the measured potency. Ceftolozane sulfate, 1147 mg, corresponds to 1000 mg ceftolozane free base.
[2]L-arginine is added as needed to achieve pH 6.5 ± 0.5; 600 mg per vial is considered a representative total amount.
[3]Actual weight of tazobactam sodium will vary based on the measured potency. Tazobactam sodium 537 mg, corresponds to 500 mg tazobactam free acid
4) Nitrogen blanket is applied after powders are dispensed to the vial and prior to insertion of stopper.

A first aqueous solution comprising the ingredients in the ceftolozane drug composition in Table 11 is lyophilized in the absence of tazobactam to provide the lyophilized ceftolozane composition. The first aqueous solution comprises ceftolozane sulfate and the specific excipients in the preferred compositions, in an amount per unit dosage form provided by the quantities and functions as provided in Table 10. All excipients are compendial and typical for sterile pharmaceutical dosage forms, requiring no additional treatment prior to use in the formulation. The excipients are used in levels within the range established in other FDA approved products as described in the Inactive Ingredients Database (IID). A second solution comprising tazobactam acid and sodium bicarbonate is lyophilized in the absence of ceftolozane to obtain the tazobactam sodium composition in Table 11. Subsequently, the lyophilized tazobactam sodium composition is dry blended with the lyophilized ceftolozane composition comprising tazobactam sodium and ceftolozane sulfate in a weight ratio providing 500 mg of tazobactam acid equivalent per 1,000 mg of ceftolozane active equivalent.

The invention claimed is:

1. A sterile pharmaceutical composition comprising tazobactam, or a pharmaceutically acceptable salt thereof, and ceftolozane, or a pharmaceutically acceptable salt thereof, in a sealed unit dosage form container, wherein the ceftolozane, or a pharmaceutically acceptable salt thereof, and the tazobactam, or a pharmaceutically acceptable salt thereof, provide ceftolozane active and tazobactam active in a ratio of 2:1 by weight, and wherein said ceftolozane, or a pharmaceutically acceptable salt thereof, and the tazobactam, or a pharmaceutically acceptable salt thereof, were not in physical contact prior to filling the composition into said unit dose form container.

2. The pharmaceutical composition of claim 1, wherein the pharmaceutically acceptable salt of ceftolozane is ceftolozane sulfate.

3. The pharmaceutical composition of claim 1, wherein the pharmaceutically acceptable salt of tazobactam is tazobactam sodium or tazobactam arginine.

4. The pharmaceutical composition of claim 3, wherein the pharmaceutically acceptable salt of tazobactam is tazobactam sodium.

5. The pharmaceutical composition of claim 1, wherein the amount of ceftolozane active is 1,000 mg and the amount of tazobactam active is 500 mg.

6. The pharmaceutical composition of claim 1, wherein the amount of ceftolozane active is 2,000 mg and the amount of tazobactam active is 1,000 mg.

7. The pharmaceutical composition of claim 1, wherein the tazobactam, or a pharmaceutically acceptable salt thereof, and the ceftolozane, or a pharmaceutically salt thereof, were individually lyophilized prior to filling.

8. The pharmaceutical composition of claim 1, wherein the unit dosage form container includes a means for injecting a liquid into the container.

9. An injectable composition for intravenous administration comprising the pharmaceutical composition of claim 1 dissolved in a pharmaceutically acceptable carrier.

10. A pharmaceutical composition comprising tazobactam, or a pharmaceutically acceptable salt thereof, and ceftolozane, or a pharmaceutically salt thereof, prepared by aseptically filling the tazobactam, or a pharmaceutically acceptable salt thereof, and the ceftolozane, or a pharmaceutically salt thereof, in a unit dosage form container and then sealing the unit dosage form container, wherein the ceftolozane, or a pharmaceutically acceptable salt thereof, and tazobactam, or a pharmaceutically acceptable salt thereof, provide ceftolozane active and tazobactam active in a ratio of 2:1 by weight.

11. The pharmaceutical composition of claim 10, wherein the unit dosage form container is blanketed with an inert gas prior to sealing.

12. The pharmaceutical composition of claim 10, wherein the ceftolozane, or a pharmaceutically acceptable salt, thereof and the tazobactam, or a pharmaceutically acceptable salt thereof, were not in physical contact prior to filling the composition into said unit dose form container.

13. The pharmaceutical composition of claim 10, wherein the tazobactam, or a pharmaceutically acceptable salt thereof, and the ceftolozane, or a pharmaceutically acceptable salt thereof, are co-filled into the unit dosage form container.

14. The pharmaceutical composition of claim 10, wherein the pharmaceutically acceptable salt of ceftolozane is ceftolozane sulfate.

15. The pharmaceutical composition of claim 10, wherein the pharmaceutically acceptable salt of tazobactam is tazobactam sodium or tazobactam arginine.

16. The pharmaceutical composition of claim 15, wherein the pharmaceutically acceptable salt of tazobactam is tazobactam sodium.

17. The pharmaceutical composition of claim 10, wherein the amount of ceftolozane active is 1,000 mg and the amount of tazobactam active is 500 mg.

18. The pharmaceutical composition of claim 10, wherein the amount of ceftolozane active is 2,000 mg and the amount of tazobactam active is 1,000 mg.

19. The pharmaceutical composition of claim 10, wherein the tazobactam, or a pharmaceutically acceptable salt thereof, and the ceftolozane, or a pharmaceutically acceptable salt thereof, were individually lyophilized prior to filling.

20. The pharmaceutical composition of claim 10, wherein the unit dosage form container includes a means for injecting a liquid into the container.

21. An injectable composition for intravenous administration comprising a pharmaceutical composition of claim 10 dissolved in a pharmaceutically acceptable carrier.

* * * * *